United States Patent
Matsui et al.

Patent Number: 5,728,319
Date of Patent: Mar. 17, 1998

[54] LIQUID CRYSTAL COMPOSITION AND LIQUID CRYSTAL DISPLAY DEVICE

[75] Inventors: Shuichi Matsui; Kazutoshi Miyazawa, both of Chiba; Noriyuki Ohnishi, Kumamoto; Yasuhiro Haseba, Chiba; Yasuyuki Goto, Chiba; Etsuo Nakagawa, Chiba; Shinichi Sawada, Chiba, all of Japan

[73] Assignee: Chisso Corporation, Osaka, Japan

[21] Appl. No.: 776,175

[22] PCT Filed: Oct. 13, 1995

[86] PCT No.: PCT/JP95/02100

§ 371 Date: Mar. 27, 1997

§ 102(e) Date: Mar. 27, 1997

[87] PCT Pub. No.: WO96/11994

PCT Pub. Date: Apr. 25, 1996

[30] Foreign Application Priority Data

Oct. 13, 1994 [JP] Japan ................... 7-205531
Oct. 13, 1994 [JP] Japan ................... 6-274511

[51] Int. Cl.⁶ .................. C09K 19/30; C09K 19/12
[52] U.S. Cl. .................. 252/299.63; 252/299.66
[58] Field of Search .................. 252/299.63, 299.66, 252/299.01

[56] References Cited

U.S. PATENT DOCUMENTS 5,045,229  9/1991  Bartmann et al. ............ 252/299.01
5,589,102  12/1996  Bartmann et al. ............ 252/299.01

*Primary Examiner*—C. H. Kelly
*Attorney, Agent, or Firm*—Wenderoth, Lind & Ponack

[57] ABSTRACT

Liquid crystal compositions are provided which have particularly a low threshold voltage, excellent miscibility at low temperatures, and a wide nematic phase range while satisfying several characteristics required of liquid crystal compositions for AM-LCD. The liquid crystal compositions contain, as a first component, at least one compound expressed by either formula (I-1) or (I-2), and as a second component, at least one compound expressed by any one of formulas (II-1) to (II-7)

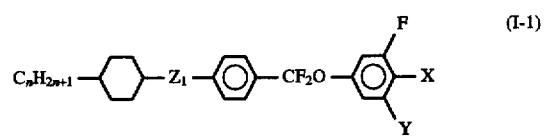

(I-1)

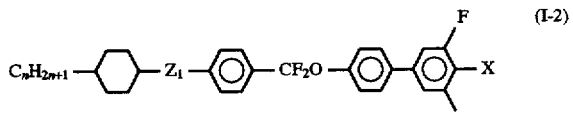

(I-2)

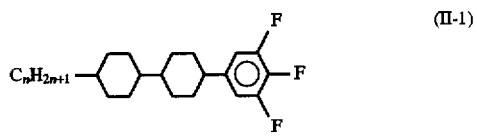

(II-1)

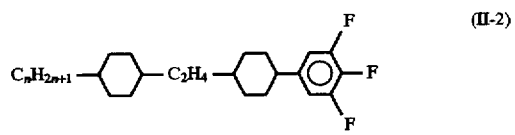

(II-2)

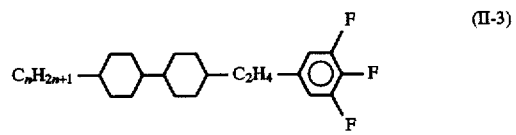

(II-3)

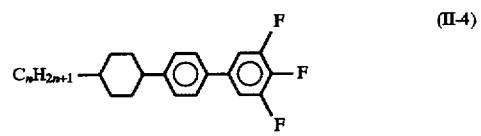

(II-4)

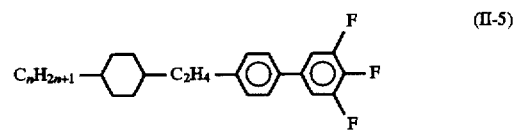

(II-5)

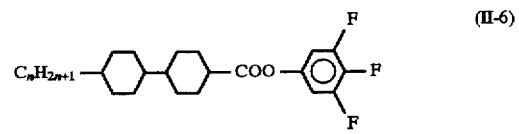

(II-6)

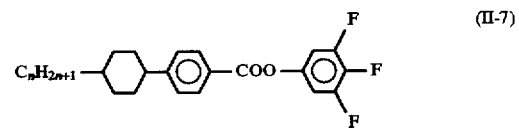

(II-7)

wherein n is an integer of 1 to 10, $Z_1$ represents —$CH_2CH_2$— or a single bond, X represents F, $OCF_3$ or $CF_3$, and Y represents H or F.

17 Claims, No Drawings

LIQUID CRYSTAL COMPOSITION AND LIQUID CRYSTAL DISPLAY DEVICE

TECHNICAL FIELD

This application is a 371 of PCT/JP95/02100 filed Oct. 13, 1995.

The present invention relates to a nematic liquid crystal composition and a liquid crystal display device using the liquid crystal composition. More specifically, the present invention relates to a liquid crystal composition for active matrix liquid crystal display device and a liquid crystal display device using the composition.

BACKGROUND ART

Since liquid crystal display device (LCD) can reduce its electric power consumption and can downsize its shape compared with CRT (cathode ray tube display), several types of LCDs such as twist nematic (TN) mode, super twist nematic (STN) mode, and thin-film transistor (TFT) mode LCDs have practically been used. Among them, active matrix LCD (AM-LCD) such as thin-film transistor (TFT) has been progressed in actualization of colored display and of fine picture image, and thus the AM-LCD has attracted public attention.

As the characteristics required of liquid crystal composition for AM-LCD, the following can be mentioned:
1) Voltage holding ratio (V.H.R) is high to maintain a high contrast of LCD.
2) Range of nematic liquid crystal phase is wide depending on application environment.
3) Appropriate optical anisotropy ($\Delta n$) can be produced depending on cell thickness.
4) Proper threshold voltage can be obtained depending on driving circuit.

As driving mode of AM-LCD, the TN display mode is adopted in which the alignment of liquid crystal molecules placed between an upper and lower substrates are twisted by 90°. In this TN display mode, the product ($\Delta n \cdot d$) of optical anisotropy ($\Delta n$) and cell thickness (d) µm must be established to a certain value (for example $\Delta n \cdot d = 0.5$ µm) to prevent the coloring of the background of the liquid crystal cell due to the interference of liquid crystal cells when voltage is not applied and to obtain a best contrast.

Under these restrictions, the value of about 0.07 to about 0.11, particularly about 0.08 to about 0.10 has become a main $\Delta n$ of the liquid crystal composition currently in practical use for TFT for the device which employs a light transmittance of about first minimum value.

Also, notebook size personal computers characterized by their portable small size and light weight have lately been developed to expand the application of LCD. LCD designed for portable size have restriction in its characteristics due to driving voltage. Since electric power consumption must be reduced to use the LCD for long period of time, liquid crystal compositions of a low threshold voltage have come to be required. Liquid crystals of a small threshold voltage have also come to be required even to make the power supply for driving the LCD light weight and low cost.

With the portable-sizing, the development with the purpose of using it outdoors has come to be studied. In order to withstand outdoor use, it is required to exhibit nematic phase over a range beyond the temperature range of application environment. From these viewpoints, liquid crystal compositions having a nematic-isotropic phase transition temperature(clearing point: $T_{NI}$) of higher than 60° C. and smectic-nematic phase transition temperature ($T_{SN}$) of lower than −20° C. have become main liquid crystal compositions currently in practical use for TFT.

With such background, trifluoro compounds having a comparatively large dielectric anisotropy ($\Delta \epsilon$) are disclosed in Japanese Patent Application Laid-open No. Hei 2-233626. Whereas a composition comprising 15% by weight of trifluoro compound and 85% by weight of difluoro compound is disclosed as an example in its Application Example 2, the composition has the defect of being short of practicability since its threshold voltage is high, miscibility is poor at low temperatures in particular, and nematic phase range is narrow.

In WO 94/03558 publication, examples of compositions comprising a trifluoro compound and a difluoro compound are disclosed. However, the compositions disclosed in its Examples 1 and 2 are as low as 50° C. or lower in clearing point, and less than 0.06 in $\Delta n$; and thus they are short of utility. Besides, the compositions disclosed in and after Example 4 have a defect of having a high threshold voltage.

Whereas liquid crystal compositions are diligently being studied depending on several purposes as mentioned above, it is a present situation that new improvements are all the time demanded.

DISCLOSURE OF THE INVENTION

An object of the present invention is particularly to provide a liquid crystal composition having a small threshold voltage, an excellent miscibility at low temperatures, and a wide nematic phase range while satisfying several characteristics required of AM-LCD mentioned above.

Physical properties of novel difluorooxymethane derivatives which can be derived from phenylbenzoate derivatives had been investigated by the present inventors to find i) that the direction of dipole moment by the polarization of two fluorine atoms in difluoromethoxy group, which is a bonding group, efficiently contributes to the increase of dielectric constant in the direction of major axis of the molecule in the difluorooxymethane derivative and produces a large dielectric anisotropy, and thus it is effective for lowering threshold voltage; and ii) that the derivatives are extremely low in viscosity.

Also, it had been found that the compounds in which fluorine containing group is selected as their terminal substituent are novel liquid crystalline compounds for low voltage useful in AM-LCD.

As a result of diligent investigation on the compositions containing such liquid crystal compounds, it has now been found that the problems mentioned above can be solved when the liquid crystal compositions of the present invention are used for AM-LCD; and thus the present invention is described in detail below.

The present invention is concerned with a liquid crystal composition containing at least one specific difluorooxymethane derivative expressed by general formula (I)

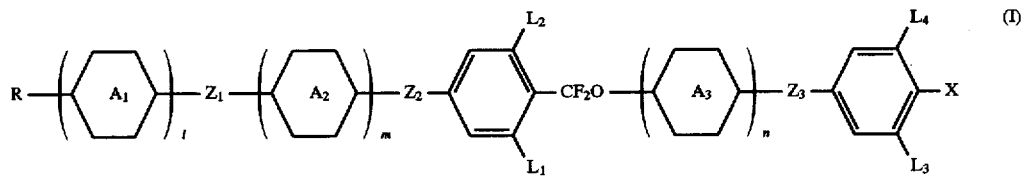

wherein l is 1, m is 0, n is 0 or 1, ring $A_1$ represents trans-1,4-cyclohexylene group, ring $A_3$ represents 1,4-phenylene group, $Z_1$ represents —$CH_2CH_2$— or a covalent bond, $Z_2$ and $Z_3$ represent a covalent bond, $L_1$ and $L_2$ represent hydrogen atom, $L_3$ represents Y (Y indicates hydrogen atom or fluorine atom), $L_4$ represents fluorine atom, R represents an alkyl group expressed by $C_nH_{2n+1}$ (n indicates an integer of 1 to 10), and X represents fluorine atom, $CF_3$, or $OCF_3$; said specific difluorooxymethane derivative being included in the compounds expressed by the same general formula (I) mentioned above wherein each of l, m, and n is 0 or 1, rings $A_1$ and $A_2$ independently represent trans-1,4-cyctohexylene group, 1,4-phenylene group one or more hydrogen atoms in which six-membered ring may be replaced by halogen atom, trans-1,3-dioxane-2,5-diyl, or pyrimidine-2,5-diyl, ring $A_3$ represents 1,4-phenylene group one or more hydrogen atoms in which six-membered ring may be replaced by halogen atom, trans-1,3-dioxane-2,5-diyl, or pyrimidine-2,5-diyl, $Z_1$, $Z_2$, and $Z_3$ independently represent a covalent bond, —$CH_2CH_2$—, —COO—, —$CF_2O$—, —$OCF_2$—, —$CH_2O$—, —$OCH_2$—, —CH=CH—, or —C≡C—, $L_1$, $L_2$, $L_3$, and $L_4$ independently represent hydrogen atom or halogen atom, respectively, X is halogen atom, CN, $CF_3$, $OCF_3$, $OCHF_2$, $OCH_2F$, or a linear or branched alkyl group, alkenyl group, or alkoxy group having 1 to 10 carbon atoms, and R is a linear or branched alkyl group or alkenyl group having 1 to 10 carbon atoms, one or not adjacent 2 or more $CH_2$ groups in the R may be replaced by oxygen atom, provided that in no case X is an alkyl group, alkenyl group, or alkoxy group except in the case where $Z_2$ is —$CF_2O$— or —$OCF_2$—.

That is, the first aspect of the present invention is concerned with a liquid crystal composition characterized by containing, as a first component, at least one compound expressed by either general formula (I-1) or (I-2) and containing, as a second component, at least one compound expressed by any one of general formulas (II-1) to (II-7).

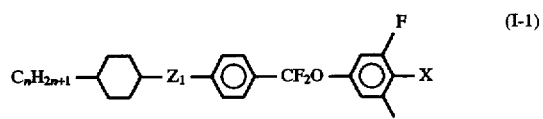

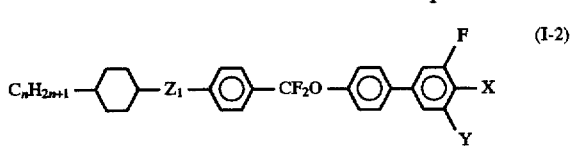

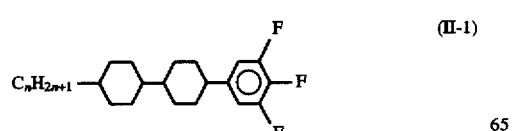

-continued

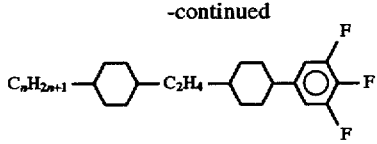

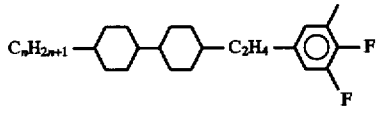

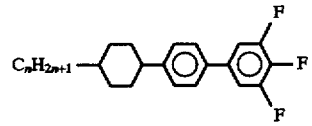

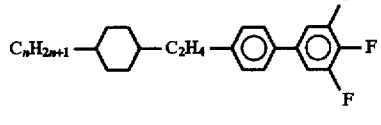

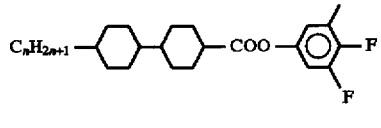

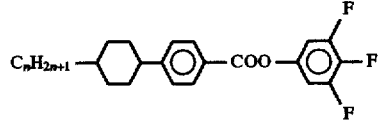

wherein n is an integer of 1 to 10, $Z_1$ represents —$CH_2CH_2$— or single bond, X represents F, $OCF_3$, or $CF_3$, and Y represents H or F.

Second aspect of the present invention is concerned with the liquid crystal composition recited in the first aspect of the present invention characterized in that the amount of the first component is 3 to 50% by weight, preferably 3 to 40% by weight and that of the second component is 50 to 97% by weight each based on the total weight of the liquid crystal composition.

Third aspect of the present invention is concerned with the liquid crystal composition characterized by further containing a compound expressed by general formula (III) in addition to the liquid crystal composition recited in the first or the second aspect of the present invention mentioned above

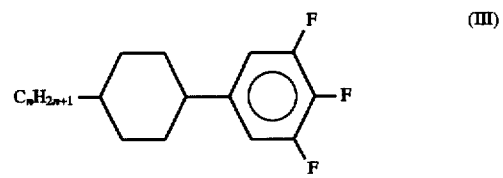

wherein n is an integer of 1 to 10.

Fourth aspect of the present invention is concerned with the liquid crystal composition characterized by containing a compound expressed by either general formula (IV-1) and/or (IV-2) in addition to the liquid crystal composition recited in any one of the first to third aspect of the present invention mentioned above

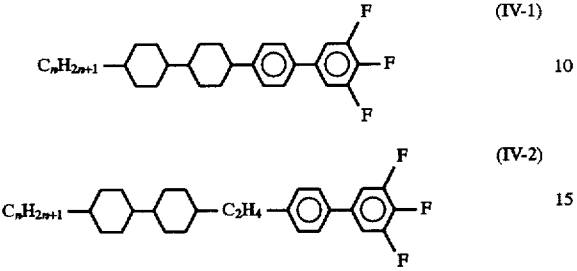

(IV-1)

(IV-2)

wherein n is an integer of 1 to 10.

Fifth aspect of the present invention is concerned with the liquid crystal composition characterized by containing a compound expressed by general formula (V-1) and/or (V-2) in addition to the liquid crystal composition recited in any one of the first to fourth aspect of the present invention mentioned above

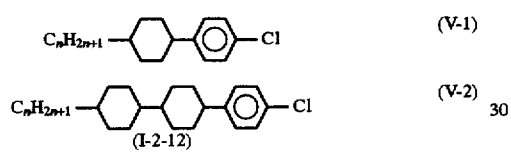

(V-1)

(V-2)

(I-2-12)

wherein n is an integer of 1 to 10.

Sixth aspect of the present invention is concerned with a liquid crystal display device which has used the liquid crystal composition recited in any one of the first to fifth aspect of the present invention mentioned above.

BEST MODE FOR CARRYING OUT THE INVENTION

Compounds composing each component in the present invention are explained below.

In the present invention, the following compounds are preferable as the ones expressed by general formula (I-1) or (I-2):

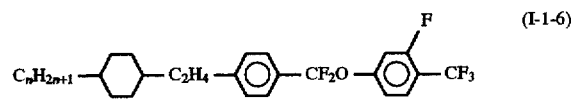
(I-1-1)

(I-1-2)

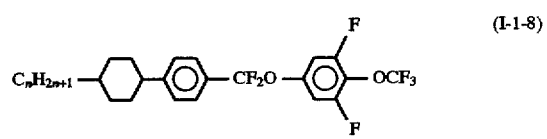
(I-1-3)

(I-1-4)

(I-1-5)

-continued

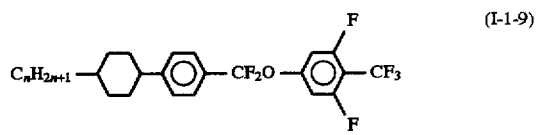
(I-1-6)

(I-1-7)

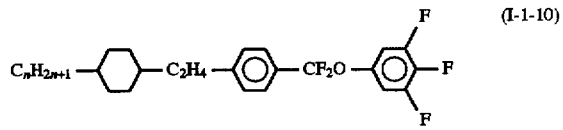
(I-1-8)

(I-1-9)

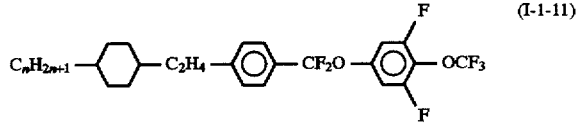
(I-1-10)

(I-1-11)

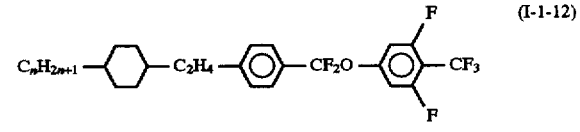
(I-1-12)

(I-2-1)

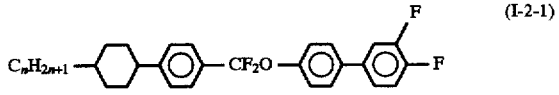
(I-2-2)

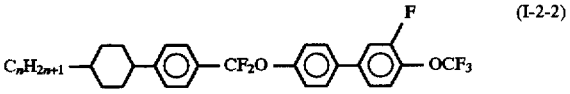
(I-2-3)

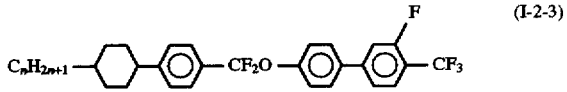
(I-2-4)

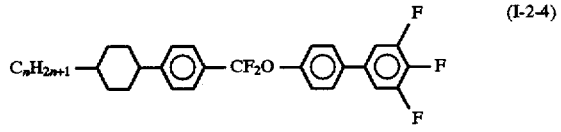
(I-2-5)

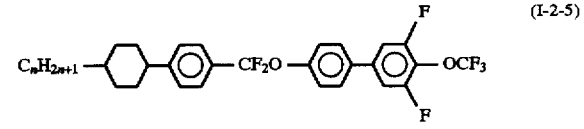

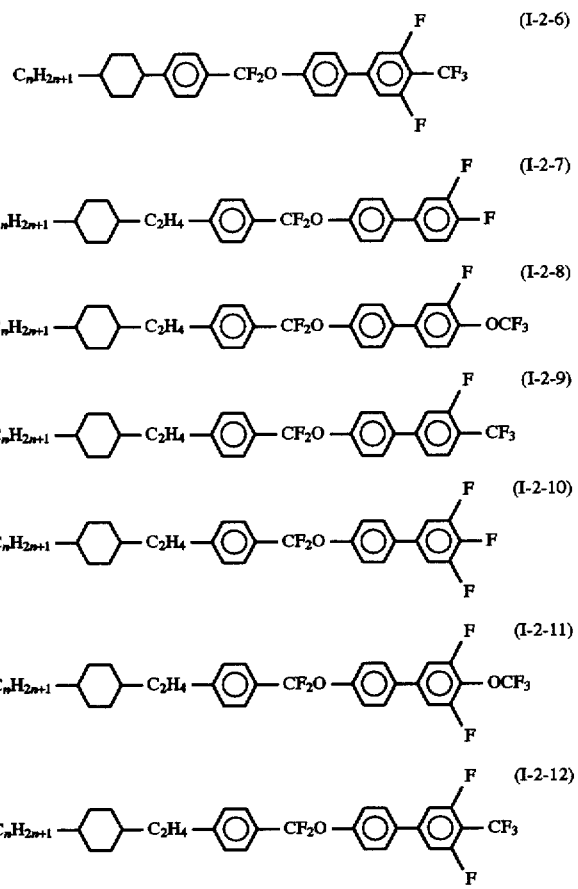

In these formulas, n is an integer of 1 to 10. In the formulas mentioned above, the compounds expressed by formula (I-1-1), (I-1-2), (I-1-5), (I-1-7), (I-1-9), (I-1-10), (I-2-4), or (I-2-12) are especially preferable.

Compounds of general formula (I-1) assume the role particularly of lowering threshold voltage of liquid crystal compositions for TFT since they have a value of dielectric anisotropy ($\Delta\epsilon$) in a range of about 9 to about 16 and are excellent in thermal and chemical stability. Compounds of general formula (I-2) assume the role of lowering the threshold voltage as well as the role of raising the clearing point of liquid crystal compositions since they are tetracyclic compounds.

Amount of the first component to be used in the present invention is preferably 3 to 40% by weight, and more desirably 5 to 35% by weight. When it is less than 3% by weight, the effect of low voltage, which is a principal subject of the present invention, is hardly obtained. When it exceeds 40% by weight, the miscibility of liquid crystal compositions becomes poor at low temperatures in some instances.

Compounds of general formulas (I-1) and (I-2) can be prepared by the procedures as follows:

First, a method for preparing a difluorooxymethane derivative expressed by general formula (I) is illustrated.

As shown in equation 1 below, a benzonitrile derivative, which is expressed by general formula (A) and used as raw material for the preparation, is hydrolyzed in an alcohol solvent such as ethyl alcohol, ethylene glycol, and diethylene glycol by using, as catalyst, a base such as sodium hydroxide and potassium hydroxide, or a mineral acid such as hydrochloric acid and sulfuric acid, to lead to a carboxylic acid derivative (B). Then, the carboxylic acid derivative (B) is reacted with a phenol derivative expressed by general formula (C) according to a general esterification method, for instance, by using, as acid catalyst, a mineral acid such as hydrochloric acid and sulfuric acid, an organic acid such as p-toluene sulfonic acid, or an ion exchange resin such as Amberite, or by using N,N'-dicyclohexylcarbodiimide (DCC) as catalyst, to prepare an ester derivative expressed by general formula (D). Also, the derivative (D) can be prepared by reacting (B) with thionyl chloride to convert into an acid chloride and then reacting with the (C) in the presence of a base such as pyridine. Subsequently, the ester derivative (D) is reacted with Lawesson reagent, [2,4-bis(4-methoxyphenyl)-1,3-dithia-2,4-diphosphetane-2,4-disulfide] (Bull. Soc. Chim. Belg., 87, 223, 229, 299, 525 (1978); Synthesis, 941 (1979); Tetrahedron, 35, 2433 (1979); Tetrahedron, Lett., 21, 4061 (1980)) by using benzene or toluene as solvent at an optional temperature from room temperature to the boiling point of the solvent to lead to a thioester (thione type) derivative (E). Then, the thioester derivative (thione type) (E) is reacted with diethylaminosulfur trifluoride (DAST) (Synthesis, 787 (1973)) by using dichloromethane or chloroform as solvent at an optional temperature from room temperature to the boiling point of the solvent for conducting gem-fluorination to prepare an objective difluorooxymethane derivative.

(Equation 1)

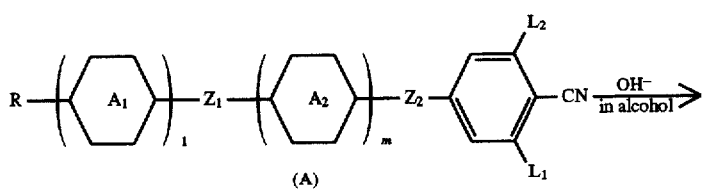

-continued
(Equation 1)

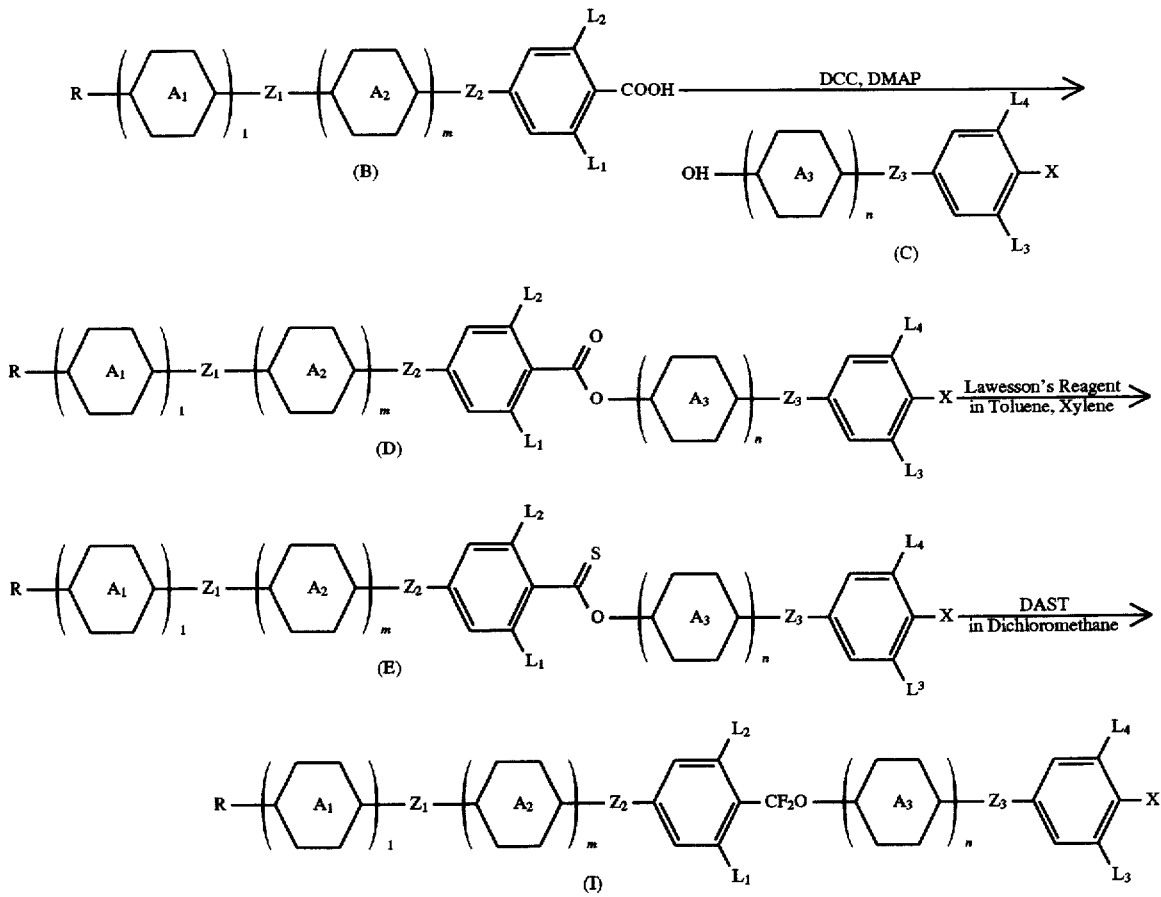

As an alternative method, as shown in equation 2 below, a difluorooxymethane derivative can be prepared by first preparing Grignard reagent from a bromobenzene derivative (F), reacting it with carbon disulfide to form a dithiocarboxylic acid derivative (G), converting it with thionyl chloride into thiocarboxylic acid chloride, reacting with a phenol derivative (C) to prepare a thioester (thione type) derivative (E), and then reacting with DAST in the same way as mentioned above.

(Equation 2)

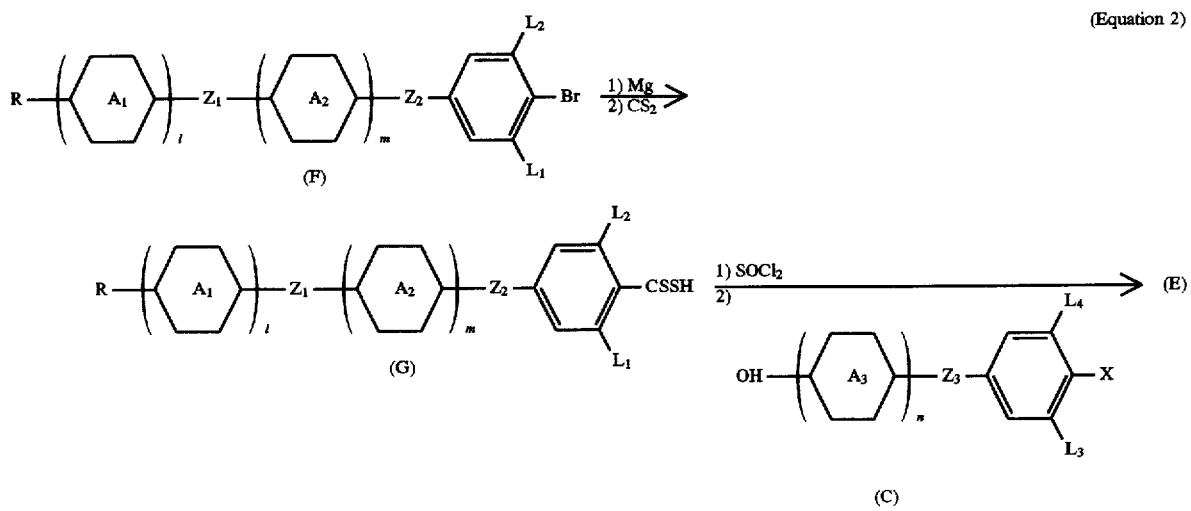

Among the compounds expressed by the general formula (I), compound (7), which is an analogue of the compounds expressed by general formula (I-1) or (I-2) and a first component in the present invention can be prepared by the method as shown in equation 3 below:

Alkylbenzoic acid derivative 1 is first subjected to an esterification with 3,4,5-trifluorophenol according to a general esterification method, for instance, by using, as acid catalyst, a mineral acid such as hydrochloric acid and sulfuric acid, an organic acid such as p-toluene sulfonic acid, or an ion exchange resin such as Amberite, or by using N,N'-dicyclohexylcarbodiimide (DCC) as catalyst to prepare 3,4,5-trifluorobenzoate derivative 2. Subsequently, the derivative 2 is reacted with Lawesson reagent under toluene refluxing condition to convert into a thioester (thione type) derivative 3, and then reacted with DAST in dichloromethane to prepare compound (7). Besides, compounds expressed by general formula (I-1) or (I-2) can be prepared from several kinds of known benzoic acid derivatives according to the preparation procedures mentioned above and by using a phenol having a different kind of substituent in place of 3,4,5-trifluorophenol.

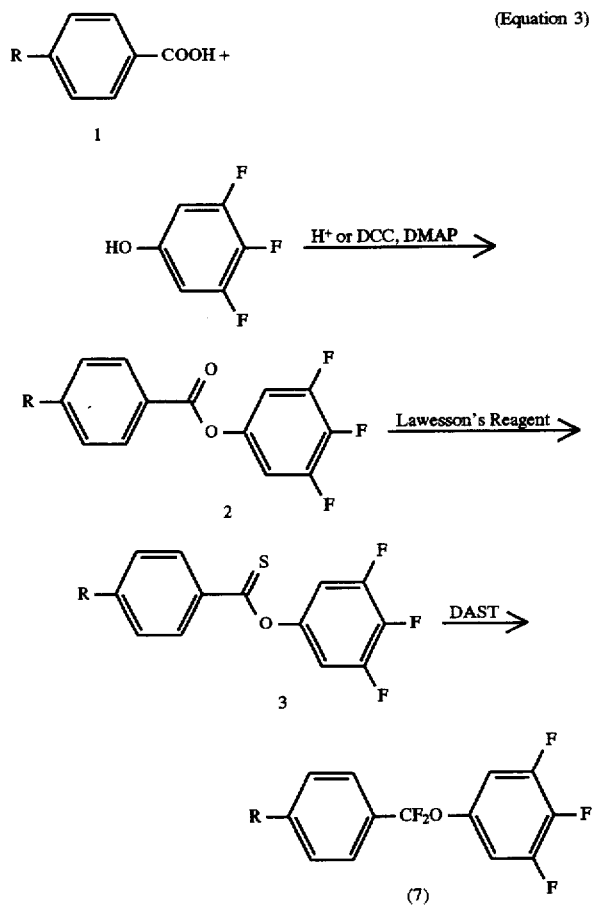

(Equation 3)

In this connection, 3,4,5-trifluorophenol, which is a raw material for the preparation, can be prepared by using 3,4,5-trifluorobromobenzene as starting material. That is, as shown in equation 4 below, it can be prepared by reacting Grignard reagent prepared from 3,4,5-trifluorobromobenzene with t-butyl hydroperoxide according to the method of S. O. Lawesson et al. (J. Am. Chem. Soc. 81, 4230 (1959)) or by treating Grignard reagent prepared from 3,4,5-trifluorobromobenzene with trialkyl borate according to the method of R. L. Kidwell et al. (Org. Synth., V, 918, (1973)) to convert into a boric acid ester and then subjecting to an oxidizing treatment with hydrogen peroxide solution.

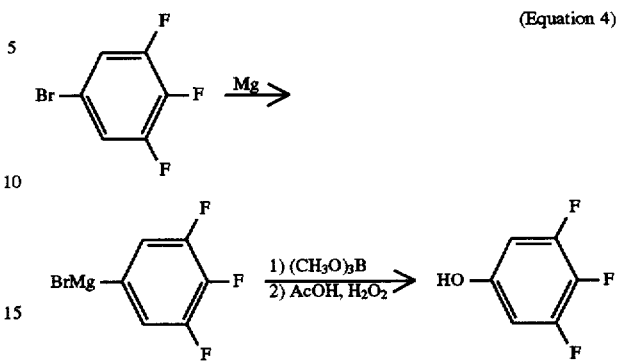

(Equation 4)

Among the compounds expressed by general formula (I-1), for example, compound (I-1-7) can be prepared by the method as shown in equation 5 below:

First, 4-(trans-4-alkylcyclohexyl)benzonitrile 4 is hydrolyzed in ethylene glycol or diethylene glycol in the presence of sodium hydroxide to convert into a benzoic acid derivative 5, and subjected to an esterification with 3,4,5-trifluorophenol according to a general esterification method, for instance, by using, as acid catalyst, a mineral acid such as hydrochloric acid and sulfuric acid, an organic acid such as p-toluene sulfonic acid, or an ion exchange resin such as Amberite, or by using N,N'-dicyclohexylcarbodiimide (DCC) as catalyst to prepare 4-trifluorobenzoate derivative 6. Subsequently, the derivative 6 is reacted with Lawesson reagent under toluene refluxing condition to convert into a thioester (thione type) derivative 7, and then reacted with DAST in dichloromethane to prepare compound (I-1-7). Besides, compounds (I-1-1) to (I-1-3), and (I-1-8) to (I-1-9) can be prepared from several kinds of known benzoic acid derivatives according to the preparation procedures mentioned above and by using phenol having a different kind of substituent in place of 3,4,5-trifluorophenol.

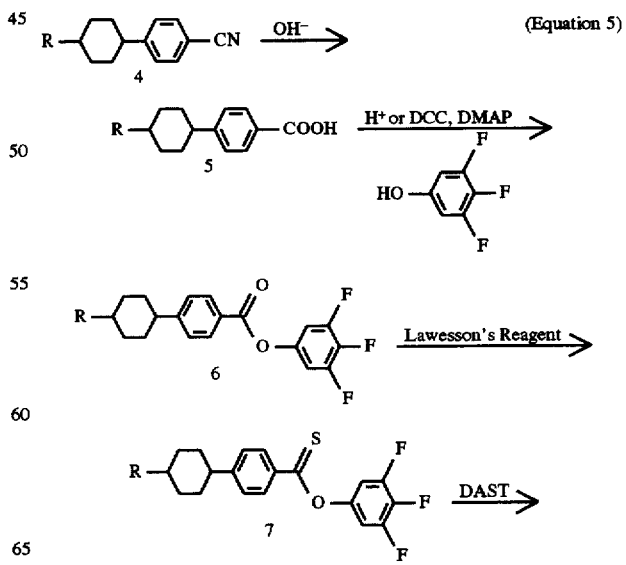

(Equation 5)

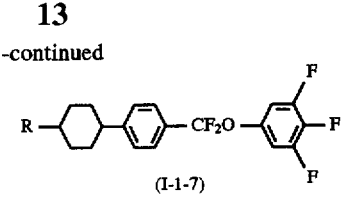

(I-1-7)

As shown in equation 6 below, for example, compound (I-2-4) among the compounds expressed by general formula (I-2) can be prepared by the following method:

That is, 4-iodobenzene is subjected to a coupling reaction with Grignard reagent prepared from 3,4,5-trifluorobromobenzene, in the presence of a novel metal catalyst such as palladium chloride to convert into a biphenyl derivative 8 and then reacted with bromine in the presence of metal powder such as iron powder to prepare a bromobiphenyl derivative 9. Subsequently, Grignard reagent prepared from the derivative 9 is reacted with trimethyl borate according to the report by R. L. Kidwell et al. (Org. Synth., V, 918 (1973)), and then oxidized with hydrogen peroxide in the presence of acetic acid to prepare a phenyl phenol derivative 10. Compound (I-2-4) can be prepared by treating the derivative 10 in the same way as in the case of the preparation of compound (7). Further, the compounds (I-2-1) to (I-2-3), (I-2-5) to (I-2-6) expressed by general formula (1c) can be prepared from phenyl phenol derivatives which were prepared by using bromobenzene derivatives having a different kind of substituent in place of 3,4,5-trifulorobromobenzene.

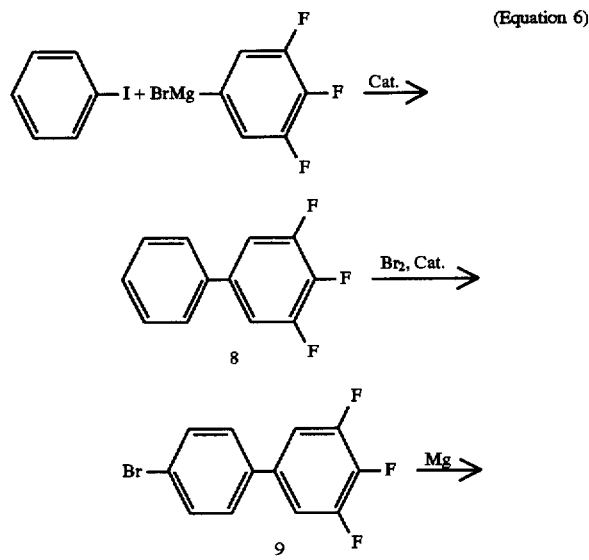

(Equation 6)

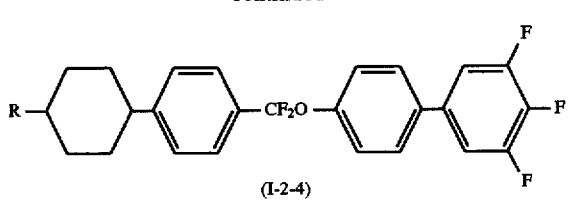

(I-2-4)

Among the compounds expressed by general formula (I-1) or (I-2), the compounds indicated by the formula wherein $Z_1$ is —$CH_2CH_2$— can be prepared by the methods as shown in equation 7 below:

First, 4-[2-(trans-4-alkylcyclohexyl)ethyl]benzoic acid 12 as raw material for the preparation can be prepared by hydrolyzing a known compound, 4-[2-(trans-4-alkylcyclohexyl)ethyl]benzonitrile 11 in ethylene glycol or diethylene glycol in the presence of sodium hydroxide. From the benzoic acid derivative 12 and one of several phenol derivatives, a phenyl benzoate derivative 13 can be prepared according to the esterification method as mentioned above. Compounds (I-1-4) to (I-1-6), (I-1-10) to (I-1-12), and (I-2-7) to (I-2-12) can be prepared by treating the phenylbenzoate derivative with Lawesson reagent in the same way as mentioned above to convert into a thioester (thione type) and then reacting with DAST.

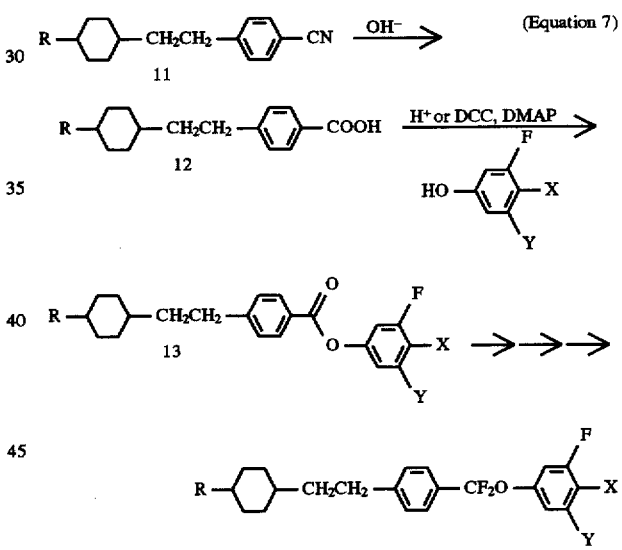

(Equation 7)

As disclosed in Japanese Patent Application Laid-open No. Hei 2-233626, trifluoro compounds of general formulas (II-1) to (II-7), (III), (IV-1), and (IV-2) are well known as compounds for low voltage TFT since they have a Δε in a range of about 7 to about 12, and are excellent in thermal stability and chemical stability (R. Tarao et al., SID 94 Digest, p 233).

Compounds of general formulas (II-1) to (II-7) have a nematic-isotropic phase transition point (clearing point: $T_{NI}$) in a range of about 50° to 100° C. and are best ones as base compound of liquid crystal composition for low voltage TFT.

Amount of the second component in the present invention is preferably 50 to 97% by weight, and more desirably 60 to 95% by weight. When the amount is less than 50% by weight, the miscibility of the liquid crystal composition becomes poor at low temperatures in some instances. When the amount exceeds 97% by weight, the effect of low voltage of the present invention is hardly obtained.

Since the compounds of general formula (III) are bicyclic trifluoro compounds, they assume the role of lowering the threshold voltage of liquid crystal compositions, in particular. Since they are bicyclic compounds, when they are used in a large amount, the clearing point of liquid crystal composition is lowered in some instances. Amount of the compounds of general formula (III) to be used is preferably less than 15% by weight, and more desirably less than 10% by weight.

Since the compounds of general formulas (IV-1) and (IV-2) are tetracyclic trifluoro compounds, they assume the role of raising clearing point of liquid crystal composition, in particular. However, when they are used in a large amount, the threshold voltage of liquid crystal composition becomes high in some instances and its miscibility may become poor at low temperatures since they are tetracyclic compound. Amount of the compounds of general formulas (IV-1) and (IV-2) is preferably less than 20% by weight, and more desirably less than 10% by weight.

Compounds of general formula (V-1) and (V-2) are bicyclic or tricyclic chlorine containing compounds. These compounds principally assume the role of reducing the viscosity of liquid crystal composition. Since Δε of the compounds is as low as 4 to 5, when they are used in a large amount, the threshold voltage of liquid crystal composition becomes high in some instances. Amount of the compounds of general formula (V) is preferably less than 30% by weight, and more desirably less than 25% by weight.

Liquid crystal compositions of the present invention may be used in a mixture with the compounds other than those expressed by the general formulas mentioned above in a range in which the objects of the present invention is not impaired.

Liquid crystal compositions used according to the present invention are prepared by conventional methods. Generally, the method is adopted in which various components are dissolved in each other at a high temperature. Also, the liquid crystal compositions of the present invention are improved to optimize, depending on the applications intended, with a suitable additive. Such additives are described in literatures. Usually, a chiral dopant or likes are added to cause a helical structure of liquid crystal to adjust a required twisting angle, and to avoid reverse-twist.

Further, the liquid crystal compositions of the present invention can be added with a dichroic dye such as merocyanine type, styryl type, azo type, azomethine type, azoxy type, quinophthalone type, anthraquinone type, and tetrazine type, and used as liquid crystal composition for guest-host (GH) mode. Alternatively, they can also be used as liquid crystal compositions for polymer dispersion type liquid crystal display devices (PDLCD) typified by NCAP which is prepared by forming a nematic liquid crystal into a microcapsule or typified by a polymer net work liquid crystal display device (PNLCD) which is prepared by forming a polymer of three-dimensional network structure in a liquid crystal. Also, the liquid crystal compositions of the present invention can be used as ones for electrically controlled birefringence (ECB) mode or dynamic scattering (DS) mode.

The present invention will be described in more detail below with reference to Examples. However, it should be understood that the present invention is by no means restricted by such specific Examples.

Preparation Examples of the compounds of general formula (I-1) and (I-2) are first described which are the first component in the liquid crystal compositions of the present invention. In each of the Examples, Cr represents crystal, N does nematic phase, S does smectic phase, SB does smetic B phase, Iso represents isotropic liquid, and the unit of every phase transition temperature is °C.

COMPOUND PREPARATION EXAMPLE 1

Preparation of difluoro-[4-(trans-4-propylcyclohexyl) phenyl]-(3,4,5-trifluorophenyloxy)methane (Compound expressed by the formula (I-1) wherein R=$C_3H_7$, $Z_1$ represents covalent bond, X=F, and Y=F)

In a 500 ml three neck distillation flask provided with a stirrer, thermometer, dropping funnel, and nitrogen gas introducing pipe, 15.0 g (60.9 mmol) of 4-(trans-4-propyl cyclohexyl)benzoic acid, 15.1 g (73.1 mmol) of DCC (N,N'-dicyclohexylcarbodiimide), and 0.3 g (2.2 mmol) of DMAP (4-dimethylaminopyridine) were dissolved in 250 ml of dichloromethane under nitrogen gas atmosphere, and then 10.8 g (73.0 mmol) of 3,4,5-trifluorophenol was added dropwise to the solution in 3 min while stirring at room temperature. After the dropping, the solution was stirred for 10 hours at room temperature. Then, 100 ml of water was added to the reaction solution. After dichloromethane insoluble matter was filtered off, the dichloromethane layer was separated and the water layer was further extracted with 200 ml of dichloromethane. Extracted layers were mixed and washed with 100 ml×2 of water, 100 ml of saturated aqueous solution of sodium hydrogencarbonate, and 100 ml×2 of water in turn, dried over anhydrous magnesium sulfate, and then concentrated under a reduced pressure to obtain 23.8 g of reaction product. Reaction product was purified by a column chromatography using silica gel as filler and using toluene as developing solvent, and further recrystallized from a mixed solvent of heptane-ethanol to obtain 13.2 g of colorless crystal product. This product was 3,4,5-trifluoro-[4-(trans-4-propylcyclohexyl)phenyl] benzoate.

Subsequently, in a 1000 ml egg-plant type flask provided with a nitrogen gas introducing pipe and cooling pipe, 13.2 g (35.2 mmol) of 3,4,5-trifluoro-[4-(trans-4-propylcyclohexyl)phenyl]benzoate obtained by the procedures mentioned above and 28.5 g (70.4 mmol) of Lawesson reagent (2,4-bis(4-methoxyphenyl)-1,3-dithia-2,4-diphosphethane-2,4-disulfide) were dissolved in 500 ml of toluene, and the solution was refluxed while stirring under nitrogen gas stream for 60 hours. After the reaction solution was cooled down to room temperature, 200 ml of water was added, the toluene layer was separated, and then the water layer was further extracted with 150 ml of toluene. Organic layers were mixed, washed with 200 ml×2 of water, 100 ml of saturated aqueous solution of sodium hydrogencarbonate, 100 ml of 10% aqueous solution of sodium hydrogensulfite, and 200×2 ml of water in turn, dried over anhydrous magnesium sulfate, and then concentrated under a reduced pressure to obtain 13.8 g of brown crystalline mixture. Reaction product was purified by a column chromatography using silica gel as filler and using heptane as developing solvent, and then recrystallized from heptane to obtain 4.7 g of yellow needle-like crystal product having a phase transition point: Cr 127.7°–128.2° C. Iso. This product was 4-(trans-4-propylcyclohexy l)phenyl carbothio acid-O-3,4,5-trifluorophenyl.

1H-NMR (CDCl3; δppm) 0.8–2.0 (16H,m), 2.57 (1H,m), 6.78 (2H,m), 7.29 (2H, d,J=8.2 Hz), and 8.23 (2H,d,J=8.2 Hz).

Subsequently, in a 100 ml egg-plant type flask provided with a nitrogen gas introducing pipe, 4.7 g (12.1 mmol) of 4-(trans-4-propylcyclohexyl)phenyl carbothio acid-O-3,4,5-trifluorophenyl was dissolved in 50 ml of dichloromethane, and then 5.9 g (36.2 mmol) of DAST (diethylaminosulfur trifluoride) was added to the solution and then the solution was stirred at room temperature for 34 hours. Reaction solution was added with 50 ml of water, the dichloromethane layer was separated, and the water layer was further extracted with 50 ml of dichloromethane. Extracted layers were mixed, washed with 50 ml×2 of water, 30 ml of saturated aqueous solution of sodium hydrogencarbonate, and 50 ml×2 of water in turn, dried over anhydrous magnesium sulfate, and then concentrated under a reduced pressure to obtain 4.3 g of colorless crystal product. Reaction product was purified by a column chromatography using silica gel as filler and using heptane as developing solvent, and then recrystallized from heptane to obtain 1.5 g of colorless needle-like crystal product (phase transition point: Cr 70.5–71.4 Iso). This product was difluoro-[4-(trans-4-propylcyclohexyl)phenyl]-(3,4,5-trifluorophenyloxy)methane.

1H-NMR (CDCl3; δppm) 0.80–2.10(16H,m), 2.60(1H, m), 6.96 (2H,m), 7.32 (2H,d,J=8.6 Hz), and 7.62 (2H,d,J=8.6 Hz).

19F-NMR (CDCl3; δppm) −66.754(2F,s,—CF2O—), −133.521(2F,d), −164.754 (1F, t).

GC-MS (CI)m/z251 (100%), 379 (M++1-HF, 34), and 125 (27).

Following compounds can be prepared according to the preparation method mentioned above by using 4-(trans-4-alkylcyclohexyl)benzoic acids having a different alkyl chain in place of 4-(trans-4-propylcycohexyl)benzoic acid:

Difluoro-[4-(trans-4-methylcyclohexyl)phenyl]-(3,4,5-trifluorophenyloxy)methane
Difluoro-[4-(trans-4-ethylcyclohexyl)phenyl]-(3,4,5-trifluorophenyloxy)methane
Difluoro-[4-(trans-4-butylcyclohexyl)phenyl]-(3,4,5-trifluorophenyloxy)methane
Difluoro-[4-(trans-4-pentylcyclohexyl)phenyl]-(3,4,5-trifluorophenyloxy)methane Cr 62.6–63.0 Iso
Difluoro-[4-(trans-4-hexylcyclohexyl)phenyl]-(3,4,5-trifluorophenyloxy)methane
Difluoro-[4-(trans-4-heptylcyclohexyl)phenyl]-(3,4,5-trifluorophenyloxy)methane
Difluoro-[4-(trans-4-octylcyclohexyl)phenyl]-(3,4,5-trifluorophenyloxy)methane
Difluoro-[4-(trans-4-nonylcyclohexyl)phenyl]-(3,4,5-trifluorophenyloxy)methane
Difluoro-[4-(trans-4-decylcyclohexyl)phenyl]-(3,4,5-trifluorophenyloxy)methane Also, the following compounds can be prepared according to the preparation method mentioned above by using several known phenol derivatives in place of 3,4,5-trifluorophenol:

Difluoro-[4-(trans-4-ethylcyclohexyl)phenyl]-(3,4-difluorophenyloxy)methane
Difluoro-[4-(trans-4-propylcyclohexyl)phenyl]-(3,4-difluorophenyloxy)methane
Difluoro-[4-(trans-4-pentylcyclohexyl)phenyl]-(3,4-difluorophenyloxy)methane Cr 42.9–43.4 N 66.2–67.5 Iso
Difluoro-[4-(trans-4-ethylcyclohexyl)phenyl]-(4-trifluoromethylphenyloxy)methane
Difluoro-[4-(trans-4-propylcyclohexyl)phenyl]-(4-trifluoromethylphenyloxy)methane
Difluoro-[4-(trans-4-butylcyclohexyl)phenyl]-(4-trifluoromethylphenyloxy)methane
Difluoro-[4-(trans-4-pentylcyclohexyl)phenyl]-(4-trifluoromethylphenyloxy)methane Cr 79.6–79.9 Iso
Difluoro-[4-(trans-4-ethylcyclohexyl)phenyl]-(4-trifluoromethoxyphenyloxy)methane
Difluoro-[4-(trans-4-propylcyclohexyl)phenyl]-(4-trifluoromethoxyphenyloxy)methane Cr 57.3–58.2 SB 70.9–72.0 N 83.1–83.5 Iso
Difluoro-[4-(trans-4-butylcyclohexyl)phenyl]-(4-trifluoromethoxyphenyloxy)methane
Difluoro-[4-(trans-4-pentylcyclohexyl)phenyl]-(4-trifluoromethoxyphenyloxy)methane Cr 68.1–68.3 SB 80.5–80.8 N 90.2–90.4 Iso
Difluoro-[4-(trans-4-ethylcyclohexyl)phenyl]-(3-fluoro-4-trifluoromethoxyphenyloxy)methane
Difluoro-[4-(trans-4-propylcyclohexyl)phenyl]-(3-fluoro-4-trifluoromethoxyphenyloxy)methane
Difluoro-[4-(trans-4-butylcyclohexyl)phenyl]-(3-fluoro-4-trifluoromethoxyphenyloxy)methane
Difluoro-[4-(trans-4-pentylcyclohexyl)phenyl]-(3-fluoro-4-trifluoromethoxyphenyloxy)methane Cr 35.9–36.3 N 61.1–61.3 Iso
Difluoro-[4-(trans-4-ethylcyclohexyl)phenyl]-(3-fluoro-4-trifluoromethylphenyloxy)methane
Difluoro-[4-(trans-4-propylcyclohexyl)phenyl]-(3-fluoro-4-trifluoromethylphenyloxy)methane
Difluoro-[4-(trans-4-butylcyclohexyl)phenyl]-(3-fluoro-4-trifluoromethylphenyloxy)methane
Difluoro-[4-(trans-4-pentylcyclohexyl)phenyl]-(3-fluoro-4-trifluoromethylphenyloxy)methane
Difluoro-[4-(trans-4-ethylcyclohexyl)phenyl]-(3,5-difluoro-4-trifluoromethoxyphenyloxy)methane
Difluoro-[4-(trans-4-propylcyclohexyl)phenyl]-(3,5-difluoro-4-trifluoromethoxyphenyloxy)methane
Difluoro-[4-(trans-4-butylcyclohexyl)phenyl]-(3,5-difluoro-4-trifluoromethoxyphenyloxy)methane
Difluoro-[4-(trans-4-pentylcyclohexyl)phenyl]-(3,5-difluoro-4-trifluoromethoxyphenyloxy)methane
Difluoro-[4-(trans-4-ethylcyclohexyl)phenyl]-(3,5-difluoro-4-trifluoromethylphenyloxy)methane
Difluoro-[4-(trans-4-propylcyclohexyl)phenyl]-(3,5-difluoro-4-trifluoromethylphenyloxy)methane
Difluoro-[4-(trans-4-butylcyclohexyl)phenyl]-(3,5-difluoro-4-trifluoromethylphenyloxy)methane
Difluoro-[4-(trans-4-pentylcyclohexyl)phenyl]-(3,5-difluoro-4-trifluoromethylphenyloxy)methane Cr 56.9–57.5 Iso

COMPOUND PREPARATION EXAMPLE 2

Preparation of difluoro-{4-[2-(trans-4-propylcyclohexyl)ethyl]phenyl}-(3,4,5-trifluorophenyloxy)methane (Compound expressed by the formula (I-1) wherein n=3, $Z_1$ represents —$CH_2CH_2$—, X=F, and Y=F)

In a 500 ml three neck distillation flask provided with a stirrer, thermometer, dropping funnel, and nitrogen gas introducing pipe, 15.0 g (54.7 mmol) of 4-[2-(trans-4-propylcyclohexyl)ethyl]benzoic acid, 13.5 g (65.6 mmol) of DCC, and 0.25 g (1.9 mmol) of DMAP were dissolved in 250 ml of dichloromethane under nitrogen gas atmosphere, and then 9.7 g (65.6 mmol) of 3,4,5-trifluorophenol was added dropwise to the solution in 3 min while stirring at room temperature. After the dropping, the solution was stirred for 15 hours at room temperature. Then, 100 ml of water was added to the reaction solution. After dichloromethane insoluble matter was filtered off, the dichloromethane layer was separated and the water layer was further extracted with 200 ml of dichloromethane. Extracted layers were mixed and washed with 100 ml×2 of water, 100 ml of saturated aqueous solution of sodium hydrogencarbonate, and 100 ml×2 of water in turn, dried over anhydrous magnesium sulfate, and then concentrated under a reduced pressure to obtain 22.5 g of reaction product. Reaction product was purified by a column chromatography using silica gel as filler and using toluene as developing solvent, and further recrystallized from a mixed solvent of heptane-ethanol to obtain 12.9 g of colorless crystal product. This product was 3,4,5-trifluorophenyl-{4-[2-(trans-4-propylcyclohexyl)ethyl]phenyl}benzoate.

Subsequently, in a 1000 ml egg-plant type flask provided with a nitrogen gas introducing pipe and cooling pipe, 12.9 g (31.9 mmol) of 3,4,5-trifluorophenyl-{4-[2-(trans-4-propylcycloh exyl)ethyl]phenyl}benzoate obtained by the procedures mentioned above and 25.8 g (63.9 mmol) of Lawesson reagent were dissolved in 500 ml of toluene, and the solution was refluxed while stirring under nitrogen gas stream for 65 hours. After the reaction solution was cooled down to room temperature, 200 ml of water was added, the toluene layer was separated, and then the water layer was further extracted with 150 ml of toluene. Organic layers were mixed, washed with 200 ml×2 of water, 100 ml of saturated aqueous solution of sodium hydrogencarbonate, 100 ml of 10% aqueous solution of sodium hydrogensulfite, and 200×2 ml of water in turn, dried over anhydrous magnesium sulfate, and then concentrated under a reduced pressure to obtain 13.3 g of brown crystalline mixture. Reaction product was purified by a column chromatography using silica gel as filler and using heptane as developing solvent, and then recrystallized from heptane to obtain 4.5 g of yellow needle-like crystal product. This product was 4-[2-(trans-4-propylcycl ohexyl)ethyl]phenyl carbothio acid-O-3,4,5-trifluorophenyl.

Cr 95.5–97.6 Iso

1H-NMR (CDCl3; δppm) 0.7–1.9(19H,m), 2.70(2H,m), 6.80(2H,m), 7.25(2H,d,J=8.3 Hz), and 8.21(2H, d,J=8.3 Hz).

Subsequently, in a 100 ml egg-plant type flask provided with a nitrogen gas introducing pipe, 4.5 g (10.8 mmol) of 4-[2-(trans-4-propylcyclohexyl)ethyl]phenyl carbothio acid-O-3,4,5-trifluorophenyl was dissolved in 50 ml of dichloromethane at room temperature, and then 5.3 g (32.6 mmol) of DAST was added to the solution and then the solution was stirred at room temperature for 40 hours. Reaction solution was added with 50 ml of water, the dichloromethane layer was separated, and the water layer was further extracted with 50 ml of dichloromethane. Extracted layers were mixed, washed with 50 ml×2 of water, 30 ml of saturated aqueous solution of sodium hydrogencarbonate, and 50 ml×2 of water in turn, dried over anhydrous magnesium sulfate, and then concentrated under a reduced pressure to obtain 3.9 g of colorless crystal product. Reaction product was purified by a column chromatography using silica gel as filler and using heptane as developing solvent, and then recrystallized from heptane to obtain 1.5 g of colorless needle-like crystal product. This product was difluoro-{4-[2-(trans-4-propylcyclohexyl)ethyl]phenyl}-(3,4,5-trifluorophenyloxy) methane.

Cr 36.8–37.5 (NI 23.5–23.7) Iso

1H-NMR (CDCl3; δppm) 0.7–2.0(19H,m), 2.68(2H,m), 6.93 (2H,m), 7.27 (2H, d,J=8.4 Hz), and 7.58 (2H, d,J=8.4 Hz).

Following compounds can be prepared according to the preparation method mentioned above by using 4-[2-(trans-4-alkylcyclohexyl)ethyl]benzoic acids having a different alkyl chain in place of 4-[2-(trans-4-propylcycohexyl)ethyl] benzoic acid:

Difluoro-{4-[2-(trans 4-methylcyclohexyl)ethyl]phenyl}-(3,4,5-trifluorophenyloxy)methane Difluoro-{4-[2-(trans-4-ethylcyclohexyl)ethyl]phenyl}-(3,4,5-trifluorophenyloxy)methane Difluoro-{4-[2-(trans-4-butylcyclohexyl)ethyl]phenyl}-(3,4,5-trifluorophenyloxy)methane Difluoro-{4-[2-(trans-4-pentylcyclohexyl)ethyl]phenyl}-(3,4,5-trifluorophenyloxy)methane Difluoro-{4-[2-(trans-4-hexylcyclohexyl)ethyl]phenyl}-(3,4,5-trifluorophenyloxy)methane Difluoro-{4-[2-(trans-4-heptylcyclohexyl)ethyl]phenyl}-(3,4,5-trifluorophenyloxy)methane Difluoro-{4-[2-(trans-4-octylcyclohexyl)ethyl]phenyl}-(3,4,5-trifluorophenyloxy)methane Difluoro-{4-[2-(trans-4-nonylcyclohexyl)ethyl]phenyl}-(3,4,5-trifluorophenyloxy)methane Difluoro-{4-[2-(trans-4-decylcyclohexyl)ethyl]phenyl}-(3,4,5-trifluorophenyloxy)methane Also, the following compounds can be prepared according to the preparation method mentioned above by using several known phenol derivatives in place of 3,4,5-trifluorophenol:

Difluoro-{4-[2-(trans-4-ethylcyclohexyl)ethyl]phenyl}-(4-trifluoromethylphenyloxy)methane Difluoro-{4-[2-(trans-4-propylcyclohexyl)ethyl]phenyl}-(4-trifluoromethylphenyloxy)methane Difluoro-{4-[2-(trans-4-butylcyclohexyl)ethyl]phenyl}-(4-trifluoromethylphenyloxy)methane Difluoro-{4-[2-(trans-4-pentylcyclohexyl)ethyl]phenyl}-(4-trifluoromethylphenyloxy)methane Difluoro-{4-[2-(trans-4-ethylcyclohexyl)ethyl]phenyl}-(4-trifluoromethoxyphenyloxy)methane Difluoro-{4-[2-(trans-4-propylcyclohexyl)ethyl]phenyl}-(4-trifluoromethoxyphenyloxy)methane Cr 60.2–60.9 N 72.6–73.2 Iso Difluoro-{4-[2-(trans-4-butylcyclohexyl)ethyl]phenyl}-(4-trifluoromethoxyphenyloxy)methane Difluoro-{4-[2-(trans-4-pentylcyclohexyl)ethyl]phenyl}-(4-trifluoromethoxyphenyloxy)methane Difluoro-{4-[2-(trans-4-ethylcyclohexyl)ethyl]phenyl}-(3-fluoro-4- trifluoromethoxyphenyloxy)methane Difluoro-{4-[2-(trans-4-propylcyclohexyl)ethyl]phenyl}-(3-fluoro-4-trifluoromethoxyphenyloxy)methane Cr 30.8–31.3 N 76.9–77.7 Iso Difluoro-{4-[2-(trans-4-butylcyclohexyl)ethyl]phenyl}-(3-fluoro-4-trifluoromethoxyphenyloxy)methane Difluoro-{4-[2-(trans-4-pentylcyclohexyl)ethyl]phenyl}-(3-fluoro-4-trifluoromethoxyphenyloxy)methane Difluoro-{4-[2-(trans-4-ethylcyclohexyl)ethyl]phenyl}-(3-fluoro-4-trifluoromethylphenyloxy)methane Difluoro-{4-[2-(trans-4-propylcyclohexyl)ethyl]phenyl}-(3-fluoro- 4-trifluoromethylphenyloxy)methane Difluoro-{4-[2-(trans-4-butylcyclohexyl)ethyl]phenyl}-(3-fluoro-4-trifluoromethylphenyloxy)methane Difluoro-{4-[2-(trans-4-pentylcyclohexyl)ethyl]phenyl}-(3-fluoro-4-trifluoromethylphenyloxy)methane Difluoro-{4-[2-(trans-4-ethylcyclohexyl)ethyl]phenyl}-(3,5-difluoro-4-trifluoromethoxyphenyloxy)methane Difluoro-{4-[2-(trans-4-propylcyclohexyl)ethyl]phenyl}-(3,5-difluoro-4-trifluoromethoxyphenyloxy)methane Difluoro-{4-[2-(trans-4-butylcyclohexyl)ethyl]phenyl}-(3,5-difluoro-4-trifluoromethoxyphenyloxy)methane Difluoro-{4-[2-(trans-4-pentylcyclohexyl)ethyl]phenyl}-(3,5-difluoro-4-trifluoromethoxyphenyloxy)methane Difluoro-{4-[2-(trans-4-ethylcyclohexyl)ethyl]phenyl}-(3,5-difluoro-4-trifluoromethylphenyloxy)methane Difluoro-{4-[2-(trans-4-propylcyclohexyl)ethyl]phenyl}-(3,5-difluoro-4-trifluoromethylphenyloxy)methane Difluoro-{4-[2-(trans-4-butylcyclohexyl)ethyl]phenyl}-(3,5-difluoro-4-trifluoromethylphenyloxy)methane Difluoro-{4-[2-(trans-4-pentylcyclohexyl)ethyl]phenyl}-(3,
5-difluoro-4-trifluoromethylphenyloxy)methane

COMPOUND PREPARATION EXAMPLE 3

Preparation of difluoro-(3',4',5'-trifluorobiphenyloxy)-[4-(trans-4-propylcyclohexyl)phenyl]methane (Compound expressed by the formula (I-2) wherein n=3, $Z_1$ represents covalent bond, X=F, and Y=F)

1) Preparation of 4-(3,4,5-trifluorophenyl)phenol

By the following procedures, 4-(3,4,5-trifulorophenyl) phenol was prepared which was a raw material for the preparation of the subject compound of the present Example. That is, in a 1000 ml three neck distillation flask provided with a stirrer, thermometer, nitrogen gas introducing pipe, dropping funnel, and cooling pipe, 7.9 g (324.2 mmol) of shavings of magnesium was added, and then a solution of 65.2 g (308.8 mmol) of 3,4,5-trifluorobromobenzene in 80 ml of tetrahydrofuran (hereinafter abbreviated as THF) was added dropwise in 50 min so that the internal temperature was maintained at 50° C. After completion of the dropping, the solution was stirred on a hot water bath while keeping the same temperature for 1 hour for ageing to prepare a Grignard reagent. Then, in a 1000 ml three neck distillation flack provided with a stirrer, thermometer, nitrogen gas introducing pipe, dropping funnel, and cooling pipe, separately provided for, 35.0.g (171.6 mmol) of iodobenzene, 1.64 g ((9.3 mmol) of palladium chloride, and 300 ml of THF were added under nitrogen gas atmosphere, and added dropwise with the Grignard reagent prepared by the procedures mentioned above in 50 min while refluxing. After the dropping, the solution was further refluxed for 3 hours, cooled down to room temperature, and then added with 200 ml of water to terminate the reaction. After insoluble matter was filtered off the solution, the solution was extracted with 300 ml×2 of toluene. Extracted layer was washed with 300 ml×3 of water, dried over anhydrous magnesium sulfate, and concentrated under a reduced pressure to obtain 38.4 g of dark brown solid. Concentrated residue was purified by a chromatography using silica gel as filler and using heptane as developing solvent, and then recrystallized from a mixed solvent of heptane-ethanol to obtain 19.0 g of colorless crystal product. This product was 3,4,5-trifluorobiphenyl.

Subsequently, the biphenyl derivative thus obtained was subjected to a bromination. That is, in a 100 ml three neck distillation flack provided with a stirrer, thermometer, nitrogen gas introducing pipe, and dropping funnel, 19.0 g (91.5 mmol) of the 3,4,5-trifluorobiphenyl prepared by the procedure mentioned above was dissolved in 200 ml of dichloromethane, cooled down to -5° C. while stirring, added with 0.26 g (4.6 mmol) of iron powder, and then added dropwise with 8.8 g (109.8 mmol) of bromine in 15 min so that the temperature of -5° to 0° C. was maintained. After the completion of the dropping, the solution was further stirred for 1 hour while maintaining the same temperature. Reaction solution was added with 200 ml of water to terminate the reaction, and then extracted with 250 ml×2 of toluene. Extracted layer was washed with 200 ml×of 4 water, dried over anhydrous magnesium sulfate, and concentrated under a reduced pressure to obtain 25.1 g of brown oily product. Concentrated residue was purified by chromatography using silica gel as filler and using heptane as developing solvent, and recrystallized from a mixed solvent of heptane-ethanol to obtain 16.6 g colorless crystal product. This product was 4-bromo-3',4',5'-trifluorobiphenyl.

With reference to the report by R. L. Kidwell et al. (Org. Synth., V, 918 (1973)), the bromobiphenyl derivative obtained by the procedures mentioned above was led to a phenylphenol derivative by the following procedures. That is, in a 300 ml three neck distillation flask provided with a stirrer, thermometer, nitrogen gas introducing pipe, and dropping funnel, 1.5 g (60.9 mmol) of shavings of magnesium was added, and a solution of 16.6 g (58.0 mmol) of 4-bromo-3',4',5'-trifluorobiphenyl in 30 ml of THF was added dropwise in 25 min so that the internal temperature was maintained at 50° C. After completion of the dropping, the solution was stirred on a hot water bath for 1 hour while keeping the same temperature for ageing to prepare a Grignard reagent. Then, the reaction solution was cooled with dry ice-acetone coolant down to -20° C., added dropwise with 7.2 g of trimethyl borate, and stirred at the same temperature for 30 min. The solution was added with 3.5 g (58.0 mmol) of acetic acid at the same temperature, raised up to 20° C., and added dropwise with 7.9 g (69.6 mmol) of 30% aqueous solution of hydrogen peroxide in 10 min so that temperature of 25° C. was maintained. Reaction solution was again cooled with the coolant down to -30° C. and added dropwise with 50 ml of 20% aqueous solution of sodium thiosulfate in 10 min to terminate the reaction. Reaction solution was extracted with 150 ml×3 of ethyl acetate, washed with 200 ml×2 of saturated brine, dried over magnesium sulfate, and then concentrated under a reduced pressure to obtain 14.5 g of brown solid product. Concentrated residue was recrystallized from a mixed solvent of heptane-toluene to obtain 10.9 g of colorless crystal product. This product was 4-(3,4,5-trifluorophenyl)phenol.

2) Preparation of difluoro-(3',4',5'-trifluorobiphenyloxy)-[4-(trans-4-propylcyclohexyl)phenyl]methane In a 500 ml three neck distillation flask provided with a stirrer, thermometer, dropping funnel, and nitrogen gas introducing pipe, 15.0 g (60.9 mmol) of 4-(trans-4-propylcyclohexyl)benzoic acid, 15.1 g (73.1 mmol) of DCC, and 0.27 g (2.2 mmol) of DMAP were dissolved in 300 ml of dichloromethane, and then a solution of 16.4 g (73.1 mmol) of the 4-(3,4,5-trifluorophenyl)phenol mentioned above in 80 ml of dichloromethane was added dropwise at room temperature in 20 min while stirring. After the dropping, the solution was stirred at room temperature for 10 hours. After the reaction solution was added with 200 ml of water, the dichloromethane insoluble matter was filtered off, the dichloromethane layer was separated, and the water layer was further extracted with 200 ml of dichoromethane. Extracted layers were mixed, washed with 200 ml×2 of water, 100 ml of saturated aqueous solution of sodium hydrogencarbonate, and 200 ml×2 of water in turn, dried over anhydrous magnesium sulfate, and then concentrated under a reduced pressure to obtain 26.9 g of reaction product. The reaction product was purified by a chromatography using silica gel as filler and using toluene as developing solvent, and further recrystallized from a mixed solvent of heptane-ethanol to obtain 22.8 g of colorless crystal product. This product was (3',4',5'-trifluorobiphenyl) -4-(trans-4-cyclohexyl)benzoate.

Subsequently, in a 1000 ml egg-plant type flask provided with a nitrogen gas introducing pipe and cooling pipe, 22.8 g (50.5 mmol) of (3',4',5'-trifluorobiphenyl)-4-(trans-4-cyclohexyl)benzoate obtained by the procedures mentioned above and 40.9 g (101.1 mmol) of Lawesson reagent were dissolved in 500 ml of toluene, and the solution was refluxed while stirring under nitrogen gas stream for 60 hours. After the reaction solution was cooled down to room temperature, 200 ml of water was added, the toluene layer was separated, and then the water layer was further extracted with 200 ml of toluene. Organic layers were mixed, washed with 200 ml×2 of water, 100 ml of saturated aqueous solution of sodium hydrogencarbonate, 100 ml of 10% aqueous solution of sodium hydrogensulfite, and 200 ml×2 of water in turn, dried over anhydrous magnesium sulfate, and then concentrated under a reduced pressure to obtain 23.4 g of brown crystalline mixture. Reaction product was purified by a column chromatography using silica gel as filler and using heptane as developing solvent, and then recrystallized from heptane to obtain 8.3 g of yellow needle-like crystal product. This product was 4-(trans-4-propylcyclohexyl)phenyl carbothio acid-O-3',4',5'-trifluorobiphenyl.

In a 100 ml egg-plant type flask provided with a nitrogen gas introducing pipe, 8.3 g (17.7 mmol) of 4-(trans-4-propylcyclohexyl)phenyl carbothio acid-O-3',4',5'-trifluorobiphenyl was dissolved in 80 ml of dichloromethane at room temperature, and then 8.5 g (53.0 mmol) of DAST was added to the solution and the solution was stirred at room temperature for 40 hours. Reaction solution was added with 50 ml of water, the dichloromethane layer was separated, and the water layer was further extracted with 50 ml of dichloromethane. Extracted layers were mixed, washed with 50.ml×2 of water, 30 ml of saturated aqueous solution of sodium hydrogencarbonate, and 50 ml×2 of water in turn, dried over anhydrous magnesium sulfate, and then concentrated under a reduced pressure to obtain 8.1 g of brown crystal product. Reaction product was purified by a column chromatography using silica gel as filler and using heptane as developing solvent, and then recrystallized from heptane to obtain 1.9 g of colorless needle-like crystal product. This product was difluoro-(3',4',5'-trifluorobiphenyloxy)-[4-(trans-4-propylcyclohexyl)phenyl]methane.

Following compounds can be prepared according to the preparation method mentioned above by using 4-(trans-4-alkylcyclohexyl)benzoic acids having a different alkyl chain in place of 4-(trans-4-propylcyclohexyl)benzoic acid:

Difluoro-(3',4',5'-trifluorobiphenyloxy)-[4-(trans-4-methylcyclohexyl)phenyl]methane
Difluoro-(3',4',5'-trifluorobiphenyloxy)-[4-(trans-4-ethylcyclohexyl)phenyl]methane
Difluoro-(3',4',5'-trifluorobiphenyloxy)-[4-(trans-4-butylcyclohexyl)phenyl]methane
Difluoro-(3',4',5'-trifluorobiphenyloxy)-[4-(trans-4-pentylcyclohexyl)phenyl]methane Cr 73.8–74.4 N 163.4–164.0 Iso
Difluoro-(3',4',5'-trifluorobiphenyloxy)-[4-(trans-4-hexylcyclohexyl)phenyl]methane
Difluoro-(3',4',5'-trifluorobiphenyloxy)-[4-(trans-4-heptylcyclohexyl)phenyl]methane
Difluoro-(3',4',5'-trifluorobiphenyloxy)-[4-(trans-4-octylcyclohexyl)phenyl]methane
Difluoro-(3',4',5'-trifluorobiphenyloxy)-[4-(trans-4-nonylcyclohexyl)phenyl]methane
Difluoro-(3',4',5'-trifluorobiphenyloxy)-[4-(trans-4-decylcyclohexyl)phenyl]methane

COMPOUND PREPARATION EXAMPLE 4

Following compounds can be prepared according to the method mentioned above, by using optionally selected several known benzoic acid derivatives and several known phenol derivatives including the compounds, preparation method of which are described in detail in the Compound Preparation Examples mentioned above, in place of 4-(trans-4-propylcyclohexyl)benzoic acid or 3',4',5'-trifulorobiphenol:

Difluoro-(4'-trifluoromethoxybiphenyloxy)-[4-(trans-4-ethylcyclohexyl)phenyl]methane
Difluoro-(4'-trifluoromethoxybiphenyloxy)-[4-(trans-4-propylcyclohexyl)phenyl]methane
Difluoro-(4'-trifluoromethoxybiphenyloxy)-[4-(trans-4-butylcyclohexyl)phenyl]methane
Difluoro-(4'-trifluoromethoxybiphenyloxy)-[4-(trans-4-pentylcyclohexyl)phenyl]methane
Difluoro-(4'-trifluoromethylbiphenyloxy)-[4-(trans-4-ethylcyclohexyl)phenyl]methane
Difluoro-(4'-trifluoromethylbiphenyloxy)-[4-(trans-4-propylcyclohexyl)phenyl]methane
Difluoro-(4'-trifluoromethylbiphenyloxy)-[4-(trans-4-butylcyclohexyl)phenyl]methane
Difluoro-(4'-trifluoromethylbiphenyloxy)-[4-(trans-4-pentylcyclohexyl)phenyl]methane
Difluoro-(3'-fluoro-4'-trifluoromethoxybiphenyloxy)-[4-(trans-4-ethylcyclohexyl)phenyl]methane
Difluoro-(3'-fluoro-4'-trifluoromethoxybiphenyloxy)-[4-(trans-4-propylcyclohexyl)phenyl]methane
Difluoro-(3'-fluoro-4'-trifluoromethoxybiphenyloxy)-[4-(trans-4-butylcyclohexyl)phenyl]methane
Difluoro-(3'-fluoro-4'-trifluoromethoxybiphenyloxy)-[4-(trans-4-pentylcyclohexyl)phenyl]methane
Difluoro-(3'-fluoro-4'-trifluoromethylbiphenyloxy)-[4-(trans-4-ethylcyclohexyl)phenyl]methane
Difluoro-(3'-fluoro-4'-trifluoromethylbiphenyloxy)-[4-(trans-4-propylcyclohexyl)phenyl]methane
Difluoro-(3'-fluoro-4'-trifluoromethylbiphenyloxy)-[4-(trans-4-butylcyclohexyl)phenyl]methane
Difluoro-(3'-fluoro-4'-trifluoromethylbiphenyloxy)-[4-(trans-4-pentylcyclohexyl)phenyl]methane
Difluoro-(3',5'-difluoro-4'-trifluoromethoxybiphenyloxy)-[4-(trans-4-ethylcyclohexyl)phenyl]methane
Difluoro-(3',5'-difluoro-4'-trifluoromethoxybiphenyloxy)-[4-(trans-4-propylcyclohexyl)phenyl]methane
Difluoro-(3',5'-difluoro-4'-trifluoromethoxybiphenyloxy)-[4-(trans-4-butylcyclohexyl)phenyl]methane
Difluoro-(3',5'-difluoro-4'-trifluoromethoxybiphenyloxy)-[4-(trans-4-pentylcyclohexyl)phenyl]methane
Difluoro-(3',5'-difluoro-4'-trifluoromethylbiphenyloxy)-[4-(trans-4-ethylcyclohexyl)phenyl]methane
Difluoro-(3',5'-difluoro-4'-trifluoromethylbiphenyloxy)-[4-(trans- 4-propylcyclohexyl)phenyl]methane
Difluoro-(3',5'-difluoro-4'-trifluoromethylbiphenyloxy)-[4-(trans-4-butylcyclohexyl)phenyl]methane
Difluoro-(3',5'-difluoro-4'-trifluoromethylbiphenyloxy)-[4-(trans-4-pentylcyclohexyl)phenyl]methane
Difluoro-(3',4',5'-trifluorobiphenyloxy)-[2-fluoro-4-(trans-4-ethylcyclohexyl)phenyl]methane
Difluoro-(3',4',5'-trifluorobiphenyloxy)-[2-fluoro-4-(trans-4-propylcyclohexyl)phenyl]methane
Difluoro-(3',4',5'-trifluorobiphenyloxy)-[2-fluoro-4-(trans-4-butylcyclohexyl)phenyl]methane
Difluoro-(3',4',5'-trifluorobiphenyloxy)-[2-fluoro-4-(trans-4-pentylcyclohexyl)phenyl]methane
Difluoro-(3',4',5'-trifluorobiphenyloxy)-{4-[2-(trans-4-ethylcyclohexyl)ethyl]phenyl}methane
Difluoro-(3',4',5'-trifluorobiphenyloxy)-{4-[2-(trans-4-propylcyclohexyl)ethyl]phenyl}methane
Difluoro-(3',4',5'-trifluorobiphenyloxy)-{4-[2-(trans-4-butylcyclohexyl)ethyl]phenyl}methane
Difluoro-(3',4',5'-trifluorobiphenyloxy)-{4-[2-(trans-4-pentylcyclohexyl)ethyl]phenyl}methane
Difluoro-(4'-trifluoromethoxybiphenyloxy)-{4-[2-(trans-4-ethylcyclohexyl)ethyl]phenyl}methane
Difluoro-(4'-trifluoromethoxybiphenyloxy)-{4-[2-(trans-4-propylcyclohexyl)ethyl]phenyl}methane
Difluoro-(4'-trifluoromethoxybiphenyloxy)-{4-[2-(trans-4-butylcyclohexyl)ethyl]phenyl}methane Difluoro-(4'-trifluoromethoxybiphenyloxy)-{4-[2-(trans-4-pentylcyclohexyl)ethyl]phenyl}methane Difluoro-(4'-trifluoromethylbiphenyloxy)-{4-[2-(trans-4-ethylcyclohexyl)ethyl]phenyl}methane Difluoro-(4'-trifluoromethylbiphenyloxy)-{4-[2-(trans-4-propylcyclohexyl)ethyl]phenyl}methane Difluoro-(4'-trifluoromethylbiphenyloxy)-{4-[2-(trans-4-butylcyclohexyl)ethyl]phenyl}methane Difluoro-(4'-trifluoromethylbiphenyloxy)-{4-[2-(trans-4-pentylcyclohexyl)ethyl]phenyl}methane Difluoro-(3',5'-difluoro-4'-trifluoromethylbiphenyloxy)-{4-[2-(trans-4-ethylcyclohexyl)ethyl]phenyl}methane Difluoro-(3',5'-difluoro-4'-trifluoromethylbiphenyloxy)-{4-[2-(trans-4-propylcyclohexyl)ethyl]phenyl}methane Cr 101.8–102.1 N 134.4–135.0 Iso Difluoro-(3',5'-difluoro-4'-trifluoromethylbiphenyloxy)-{4-[2-(trans-4-butylcyclohexyl)ethyl]phenyl}methane Difluoro-(3',5'-difluoro-4'-trifluoromethylbiphenyloxy)-{4-[2-(trans-4-pentylcyclohexyl)ethyl]phenyl}methane Next, Examples and Comparative Examples of the liquid crystal compositions of the present invention are described. In the Examples and Comparative Examples, every ratio of the compound in the compositions are shown by "% by weight" Further, the compounds used in the Examples and Comparative Examples are designated by symbols based on the definition shown in Table 1.

TABLE 1

Method for Designating Compounds Using Symbols
$R-(A_1)-Z_1-\ldots-Z_n-(A_n)-X$

| 1) Left side terminal group R — | Symbol |
|---|---|
| $C_nH_{2n+1}-$ | n- |
| $C_nH_{2n+1}O-$ | nO— |
| $C_nH_{2n+1}OC_mH_{2m}-$ | nOm- |
| $CH_2=CHC_nH_{2n}-$ | Vn- |
| $C_nH_{2n+1}CH=CHC_mH_{2m}-$ | nVm- |
| $C_nH_{2n+1}CH=CHC_mH_{2m}CH=CHC_kH_{2k}-$ | nVmVk- |

| 2) Ring structure $-(A_1)-$, $-(A_n)-$ | Symbol |
|---|---|
| 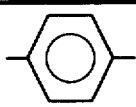 | B |
| 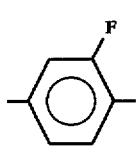 | B(F) |
| 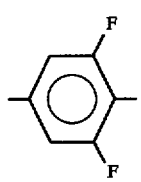 | B(F,F) |
| 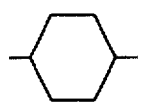 | H |

TABLE 1-continued

Method for Designating Compounds Using Symbols
$R-(A_1)-Z_1-\ldots-Z_n-(A_n)-X$

| | Symbol |
|---|---|
| (pyridine ring with two N) | Py |
| (dioxane ring with two O) | D |
| (cyclohexane ring) | Ch |

| 3) Bonding group $-Z_1-$, $-Z_n-$ | Symbol |
|---|---|
| $-CH_2CH_2-$ | 2 |
| $-COO-$ | E |
| $-C\equiv C-$ | T |
| $-CH=CH-$ | V |
| $-CF_2O-$ | CF2O |

| 4) Right side terminal group — X | Symbol |
|---|---|
| —F | —F |
| —Cl | —CL |
| —CN | —C |
| —CF$_3$ | —CF3 |
| —OCF$_3$ | —OCF3 |
| —OCF$_2$H | —OCF2H |
| —C$_n$H$_{2n+1}$ | -n |
| —OC$_n$H$_{2n+1}$ | —On |
| —COOCH$_3$ | —EMe |

5) Example of symbol

Ex. 1

3-H2B(F,F)B(F)—F

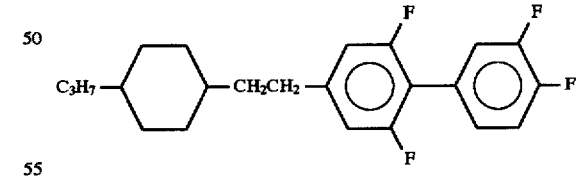

Ex. 2

3-HB(F)TB-2

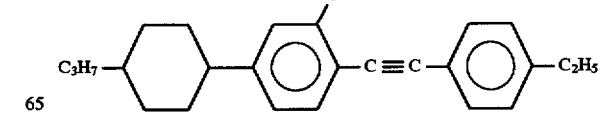

TABLE 1-continued

Method for Designating Compounds Using Symbols
R−(−A₁−)−Z₁− ... −Zₙ−(−Aₙ−)−X

Ex. 3

IV2-BEB(F,F)−C

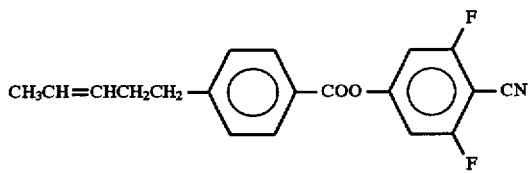

Data on the characteristics of liquid crystal compositions are shown by clearing point ($T_{NI}$), smectic-nematic phase transition point ($T_{SN}$), viscosity at 20° C. ($\eta_{20}$), optical anisotropy at 25° C. ($\Delta n$), dielectric anisotropy at 25° C. ($\Delta\epsilon$), and threshold voltage at 20° C. ($V_{th}$).

Voltage holding ratio was determined based on "Area Method" (method reported in Tatsuo Shimasaki et al., "Voltage Holding Characteristics I of TFT-LCD", Abstracts of Presentation for 14th Seminar on Liquid Crystals, p 78 (1988)), and actual determination was carried out at 25° C. at a frame period of 60 Hz, voltage of 5.0 volt, and ON time of 60 μsec; using a liquid crystal cell in which thickness of liquid crystal layer was 7.0 μm and a polyimide type alignment film was formed by a rubbing method on a substrate on which an ITO pattern having an electrode area of 1 cm² was evaporated.

$T_{SN}$ point was judged by liquid crystal phases after liquid crystal compositions were left in each of freezers at 0° C., −10° C., −20° C., and −30° C., respectively, for 30 days.

COMPARATIVE EXAMPLE 1

Following composition disclosed in Application Example 2 of Japanese Patent Application Laid-open No. Hei 2-233626 was prepared:
3 HHB(F,F)-F 15.0%
2-HHB(F) F 28.4%
3-HHB(F)-F 28.3%
5-HHB(F) F 28.3%
Physical properties of this liquid crystal composition are shown below:
$T_{NI}$=110.7° C.
$T_{SN}$<0° C.
$\eta_{20}$=25.0 mPa.s
$\Delta n$=0.077
$V_{th}$=2.32 (V)
V.H.R.=98.8%
This liquid crystal composition had a large threshold voltage and was poor in miscibility at low temperatures ($T_{SN}$ was high).

COMPARATIVE EXAMPLE 2

Following composition disclosed in Example 1 of WO 94/03558 was prepared:
7 HB(F,F) F 10.0%
2-HHB(F,F) F 25.0%
3-HHB(F,F) F 35.0%
5-HHB(F,F) F 18.0%
7 HB(F) F 12.0%
Physical properties of this liquid crystal composition are shown below:

$T_{NI}$=42.9° C.
$T_{SN}$<0° C.
$\eta_{20}$=22.2 mPa.s
$\Delta n$=0.059
$V_{th}$=1.07 (V)
V.H.R.=98.7%

Whereas this liquid crystal composition had a law threshold voltage, it was low in clearing point and poor in miscibility at low temperatures. Besides, this composition was small in Δn. Thus, the composition is insufficient in practicability.

COMPARATIVE EXAMPLE 3

Following composition disclosed in Example 2 of WO 94/03558 was prepared:
2-HHB(F,F)-F 26.0%
3-HHB(F,F)-F 26.0%
5-HHB(F,F)-F 26.0%
7-HB(F)-F 12.0%
5-H2B(F)-F 10.0%
Physical properties of this liquid crystal composition are shown below:
$T_{NI}$=46.0° C.
$T_{SN}$<0° C.
$\eta_{20}$=21.6 mPa.s
$\Delta n$=0.058
$V_{th}$=1.17 (V)
V.H.R.=98.5%

Whereas this liquid crystal composition had a law threshold voltage, it was low in clearing point and poor in miscibility at low temperatures. Besides, this composition was small in Δn. Thus, the composition is insufficient in practicability.

COMPARATIVE EXAMPLE 4

Following composition disclosed in Example 4 of WO 94/03558 was prepared:
2-HHB(F,F)-F 10.0%
3-HHB(F,F)-F 10.0%
5-HHB(F,F)-F 10.0%
5-H2B(F)-F 10.0%
5-HEB-F 7.5%
7-HEB-F 7.5%
2-HHB(F)-F 11.7%
3-HHB(F)-F 11.7%
5-HHB(F)-F 11.6%
3-HEB-F 5.0%
5-HHEB-F 2.5%
7-HHEB-F 2.5%
Physical properties of this liquid crystal composition are shown below:
$T_{NI}$=71.3° C.
$T_{SN}$<−20° C.
$\eta_{20}$=19.2 mPa.s
$\Delta n$=0.070
$V_{th}$=1.77 (V)
V.H.R.=98.2%

This liquid crystal composition had a high threshold voltage compared to its clearing point of about 70° C. Besides, Δn of the composition was slightly small.

EXAMPLE 1

3-HBCF2OB(F,F)-F 5.0%
3-H2HB(F,F)-F 7.0%
5-H2HB(F,F)-F 11.0%
3-HHB(F,F)-F 10.0%

4-HHB(F,F)-F 6.0%
3-HH2B(F,F)-F 12.0%
5-HH2B(F,F)-F 8.0%
3-HBB(F,F)-F 14.0%
5-HBB(F,F)-F 14.0%
3-HHEB(F,F)-F 9.0%
5-HHEB(F,F)-F 4.0%

Physical properties of this liquid crystal composition are shown below:
$T_{NI}$=77.2° C.
$T_{SN}$<-30° C.
$\eta_{20}$=27.4 mPa.s
$\Delta n$=0.089
$\Delta\epsilon$=9.5
$V_{th}$=1.54 (V)
V.H.R.=98.5%

This liquid crystal composition was excellent in miscibility at low temperatures, wide in nematic phase range, and small in threshold voltage. Thus, the composition of this Example is sufficient in practicability.

EXAMPLE 2

5-HBCF2OB(F)-OCF3 5.0%
3-HBCF2OB(F,F)-F 2.0%
5-HBCF2OB(F,F)-F 6.0%
3-H2BCF2OBB(F,F)-CF3 2.0%
7-HB(F,F)-F 5.0%
3-HHB(F,F)-F 7.0%
3-HH2B(F,F)-F 6.0%
3-HBB(F,F)-F 10.0%
5-HBB(F,F)-F 15.0%
2-H2BB(F,F)-F 4.0%
5-H2BB(F,F)-F 4.0%
3-HBEB(F,F)-F 3.0%
4-HBEB(F,F)-F 3.0%
5-HBEB(F,F)-F 3.0%
3-HHEB(F,F)-F 15.0%
4-HHEB(F,F)-F 5.0%
5-HHEB(F,F)-F 5.0%

Physical properties of this liquid crystal composition are shown below:
$T_{NI}$=66.3° C.
$T_{SN}$<-10° C.
$\eta_{20}$=31.1 mPa.s
$\Delta n$=0.094
$\Delta\epsilon$=11.3
$V_{th}$=1.26 (V)
V.H.R.=98.6%

This liquid crystal composition was excellent in miscibility at low temperatures, wide in nematic phase range, and small in threshold voltage. Thus, the composition of this Example is sufficient in practicability.

EXAMPLE 3

5-HBCF2OB(F)-F 5.0%
5-HBCF2OB(F)-OCF3 8.0%
3-HBCF2OB(F,F)-F 7.0%
3-HBB(F,F)-F 12.0%
5-HBB(F,F)-F 12.0%
3-HHB(F,F)-F 4.0%
3-H2BB(F,F)-F 8.0%
4-H2BB(F,F)-F 8.0%
5-H2BB(F,F)-F 8.0%
3-HBEB(F,F)-F 4.0%
3-HHEB(F,F)-F 12.0%
4-HHEB(F,F)-F 4.0%
5-HHEB(F,F)-F 4.0%
3-HH2BB(F,F)-F 4.0%

Physical properties of this liquid crystal composition are shown below:
$T_{NI}$=72.6° C.
$T_{SN}$<-30° C.
$\eta_{20}$=30.5 mPa.s
$\Delta n$=0.106
$\Delta\epsilon$=10.5
$V_{th}$=1.44 (V)
V.H.R.=98.7%

This liquid crystal composition was excellent in miscibility at low temperatures, wide in nematic phase range, and small in threshold voltage. Thus, the composition of this Example is sufficient in practicability.

EXAMPLE 4

3-HBCF2OB(F,F)-F 5.0%
5-HBCF2OB(F,F)-F 5.0%
5-HBCF2OB(F,F)-CF3 5.0%
3-HBB(F,F)-F 18.0%
5-HBB(F,F)-F 18.0%
5-H2BB(F,F)-F 10.0%
3-HBEB(F,F)-F 4.0%
3-HHEB(F,F)-F 10.0%
3-HB-CL 6.0%
2-HHB-CL 4.0%
4-HHB-CL 10.0%
5-HHB-CL 5.0%

Physical properties of this liquid crystal composition are shown below:
$T_{NI}$=77.4° C.
$T_{SN}$<-20° C.
$\eta_{20}$=25.6 mPa.s
$\Delta n$=0.111
$\Delta\epsilon$=9.7
$V_{th}$=1.58 (V)
V.H.R.=98.5%

This liquid crystal composition was excellent in miscibility at low temperatures, wide in nematic phase range, and small in threshold voltage. Thus, the composition of this Example is sufficient in practicability.

EXAMPLE 5

5-HBCF2OB(F,F)-F 10.0%
5-HBCF2OB(F)-OCF3 10.0%
7-HB(F,F)-F 8.0%
3-HHB(F,F)-F 8.0%
4-HHB(F,F)-F 4.0%
3-H2HB(F,F)-F 10.0%
4-H2HB(F,F)-F 10.0%
3-HH2B(F,F)-F 10.0%
5-HH2B(F,F)-F 8.0%
3-HBB(F,F)-F 8.0%
5-HBB(F,F)-F 8.0%
3-HHBB(F,F)-F 3.0%
3-HH2BB(F,F)-F 3.0%

Physical properties of this liquid crystal composition are shown below:
$T_{NI}$=65.2° C.
$T_{SN}$<-30° C.
$\eta_{20}$=25.8 mPa.s
$\Delta n$=0.084
$\Delta\epsilon$=8.5
$V_{th}$=1.51 (V)
V.H.R.=98.6%

This liquid crystal composition was excellent in miscibility at low temperatures, wide in nematic phase range, and

EXAMPLE 6

3-H2BCF2OB(F,F)-F 2.0%
3-HBCF2OB(F,F)-F 4.0%
5-HBCF2OB(F,F)-CF3 4.0%
3-HHB(F,F)-F 10.0%
3-HBB(F,F)-F 15.0%
5-HBB(F,F)-F 15.0%
3-H2BB(F,F)-F 10.0%
5-H2BB(F,F)-F 10.0%
3-HB-CL 10.0%
5-HB-CL 3.0%
7-HB(F,F)-F 3.0%
4-HHB-CL 5.0%
5-HHB-CL 6.0%
3-HH2BB(F,F)-F 3.0%

Physical properties of this liquid crystal composition are shown below:
$T_{NI}$=58.4° C.
$T_{SN}$<−30° C.
$\eta_{20}$=23.0 mPa.s
$\Delta n$=0.102
$\Delta \epsilon$=7.7
$V_{th}$=1.50 (V)
V.H.R.=98.6%

This liquid crystal composition was excellent in miscibility at low temperatures, wide in nematic phase range, and small in threshold voltage. Thus, the composition of this Example is sufficient in practicability.

EXAMPLE 7

3-HBCF2OB(F,F)-F 5.0%
5-HBCF2OB(F,F)-F 10.0%
5-HBCF2OB(F)-OCF3 10.0%
3-H2BCF2OBB(F,F)-CF3 5.0%
3-HHB(F,F)-F 6.0%
4-HHB(F,F)-F 4.0%
3-H2HB(F,F)-F 6.0%
4-H2HB(F,F)-F 5.0%
5-H2HB(F,F)-F 5.0%
3-HBB(F,F)-F 14.0%
5-HBB(F,F)-F 14.0%
3-HH2B(F,F)-F 10.0%
5-HH2B(F,F)-F 6.0%

Physical properties of this liquid crystal composition are shown below:
$T_{NI}$=65.0° C.
$T_{SN}$<−10° C.
$\eta_{20}$=27.9 mPa.s
$\Delta n$=0.094
$\Delta \epsilon$=9.8
$V_{th}$=1.47 (V)
V.H.R.=98.7%

This liquid crystal composition was excellent in miscibility at low temperatures, wide in nematic phase range, and small in threshold voltage. Thus, the composition of this Example is sufficient in practicability.

EXAMPLE 8

3-H2BCF2OBB(F,F)-CF3 10.0%
3-H2HB(F,F)-F 10.0%
4-H2HB(F,F)-F 10.0%
5-H2HB(F,F)-F 10.0%
3-HHB(F,F)-F 8.0%
3-HH2B(F,F)-F 7.0%
5-HH2B(F,F)-F 7.0%
3-HBB(F,F)-F 12.0%
5-HBB(F,F)-F 11.0%
2-HHB(F)-F 1.6%
3-HHB(F)-F 1.7%
5-HHB(F)-F 1.7%
2-HBB(F)-F 1.3%
3-HBB(F)-F 1.3%
5-HBB(F)-F 2.4%
3-HB(F)VB-2 5.0%

Physical properties of this liquid crystal composition are shown below:
$T_{NI}$=91.0° C.
$T_{SN}$<−30° C.
$\eta_{20}$=33.9 mPa.s
$\Delta n$=0.106
$\Delta \epsilon$=9.2
$V_{th}$=1.75 (V)
V.H.R.=98.7%

This liquid crystal composition was excellent in miscibility at low temperatures and wide in nematic phase range, and small in threshold voltage compared to its clearing point of about 90° C. Besides, it had a properly large $\Delta n$. Thus, the composition of this Example is sufficient in practicability.

EXAMPLE 9

3-HBCF2OB(F,F)-F 5.0%
5-HBCF2OB(F,F)-F 10.0%
7-HB(F,F)-F 4.0%
3-HBB(F,F)-F 12.0%
5-HBB(F,F)-F 12.0%
3-HHB(F,F)-F %
3-H2BB(F,F)-F 9.0%
4-H2BB(F,F)-F 9.0%
5-H2BB(F,F)-F 9.0%
3-HBEB(F,F)-F 3.0%
3-HHEB(F,F)-F 12.0%
4-HHEB(F,F)-F 4.0%
5-HHEB(F,F)-F 4.0%
2-HHHB(F,F)-F 3.0%

Physical properties of this liquid crystal composition are shown below:
$T_{NI}$=60.6° C.
$T_{SN}$<−20° C.
$\eta_{20}$=29.3 mPa.s
$\Delta n$=0.098
$\Delta \epsilon$=11.1
$V_{th}$=1.31 (V)
V.H.R.=98.6%

This liquid crystal composition was excellent in miscibility at low temperatures, wide in nematic phase range, small in threshold voltage. Thus, the composition of this Example is sufficient in practicability.

EXAMPLE 10

3-HBCF2OB(F,F)-F 5.0%
5-HBCF2OB(F,F)-F 10.0%
7-HB(F,F)-F 4.0%
3-HBB(F,F)-F 12.0%
5-HBB(F,F)-F 12.0%
3-HHB(F,F)-F 4.0%
3-H2BB(F,F)-F 9.0%
4-H2BB(F,F)-F 13.0%
5-H2BB(F,F)-F 9.0%
2-HBEB(F,F)-F 3.0%
2-HH2B(F,F)-F 12.0%

3-HH2BB(F,F)-F 4.0%
2-HHHB(F,F)-F 3.0%

Physical properties of this liquid crystal composition are shown below:

$T_{NI}$=54.9° C.
$T_{SN}$<-30° C.
$\eta_{20}$=31.0 mPa·s
$\Delta n$=0.122
$\Delta\epsilon$=9.3
$V_{th}$=1.29 (V)
V.H.R.=98.5%

This liquid crystal composition was excellent in miscibility at low temperatures, wide in nematic phase range, small in threshold voltage. Thus, the composition of this Example is sufficient in practicability.

Examples other compositions of the present invention are mentioned below:

EXAMPLE 11

3-HBCF2OB(F)-F 10.0%
5-HBCF2OBB(F)-F 10.0%
7-HB(F,F)-F 5.0%
3-HHB(F,F)-F 5.0%
3-H2HB(F,F)-F 5.0%
3-HBB(F,F)-F 15.0%
5-HBB(F,F)-F 11.0%
3-H2BB(F,F)-F 5.0%
4-H2BB(F,F)-F 5.0%
5-H2BB(F,F)-F 5.0%
4-HBEB(F,F)-F 3.0%
5-HBEB(F,F)-F 3.0%
3-HHEB(F,F)-F 8.0%
4-HHEB(F,F)-F 5.0%
5-HHEB(F,F)-F 5.0[{]jf44bEXAMPLE 12
3-H2BCF2OB(F)-OCF3 10.0%
3-H2BCF2OB(F,F)-F 7.0%
3-H2HB(F,F)-F 8.0%
5-H2HB(F,F)-F 7.0%
3-HHB(F,F)-F 10.0%
4-HHB(F,F)-F 4.0%
3-HH2B(F,F)-F 10.0%
5-HH2B(F,F)-F 5.0%
3-HBB(F,F)-F 15.0%
5-HBB(F,F)-F 10.0%
3-HHEB(F,F)-F 8.0%
5-HHEB(F,F)-F 2.0%
3-HHBB(F,F)-F 2.0%
3-HH2BB(F,F)-F 2.0[{]jf44bEXAMPLE 13
3-H2BCF2OB(F)-OCF3 10.0%
5-HBCF2OBB(F,F)-F 3.0%
3-H2HB(F,F)-F 12.0%
5-H2HB(F,F)-F 11.0%
3-HHB(F,F)-F 10.0%
4-HHB(F,F)-F 6.0%
3-HH2B(F,F)-F 12.0%
5-HH2B(F,F)-F 8.0%
3-HBB(F,F)-F 14.0%
5-HBB(F,F)-F 14.0%

Characteristics of the liquid crystal compositions of the Comparative Examples and Examples mentioned above are shown in Table 2. As clearly seen from Table 2, liquid crystal compositions can be provided according to the present invention which are low in threshold voltage, excellent in miscibility at low temperatures, and wide in nematic phase range while satisfying several characteristics required of liquid crystal compositions for AM-LCD.

TABLE 2

Characteristics of Liquid Crystal Compositions in Comparative Examples and Examples

|  | Comp. Ex. 1 | Comp. Ex. 2 | Comp. Ex. 3 | Comp. Ex. 4 | Ex. 1 | Ex. 2 | Ex. 3 |
|---|---|---|---|---|---|---|---|
| TNI (°C.) | 110.7 | 42.9 | 46.0 | 71.3 | 77.2 | 66.3 | 72.6 |
| TSN (°C.) | <0 | <0 | <0 | <-20 | <-30 | <-10 | <-30 |
| η20 (mPa·s) | 25.0 | 22.2 | 21.6 | 19.2 | 27.4 | 31.1 | 30.5 |
| Δn | 0.077 | 0.059 | 0.058 | 0.070 | 0.089 | 0.094 | 0.106 |
| Vth (V) | 2.32 | 1.07 | 1.17 | 1.77 | 1.54 | 1.26 | 1.44 |
| V.H.R. (%) | 98.8 | 98.7 | 98.5 | 98.2 | 98.5 | 98.6 | 98.7 |

|  | Ex. 4 | Ex. 5 | Ex. 6 | Ex. 7 | Ex. 8 | Ex. 9 | Ex. 10 |
|---|---|---|---|---|---|---|---|
| TNI (°C.) | 77.4 | 65.2 | 58.4 | 65.0 | 91.0 | 60.6 | 54.9 |
| TSN (°C.) | <-20 | <-30 | <-30 | <-10 | <-30 | <-20 | <-30 |
| η20 (mPa·s) | 25.6 | 25.8 | 23.0 | 27.9 | 33.9 | 29.3 | 31.0 |
| Δn | 0.111 | 0.084 | 0.102 | 0.094 | 0.106 | 0.098 | 0.122 |
| Vth (V) | 1.58 | 1.51 | 1.50 | 1.47 | 1.75 | 1.31 | 1.29 |
| V.H.R. (%) | 98.5 | 98.6 | 98.6 | 98.7 | 98.7 | 98.6 | 98.5 |

INDUSTRIAL APPLICABILITY

Liquid crystal compositions of the present invention are useful as liquid crystal material for low voltage in several modes such as active matrix mode and STN mode.

We claim:

1. A liquid crystal composition containing, as a first component, at least one compound expressed by general formula (I-1) or (I-2), and containing, as a second component, at least one compound expressed by any one of general formulas (II-1) to (II-7)

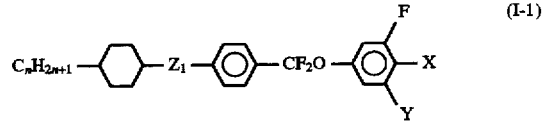
(I-1)

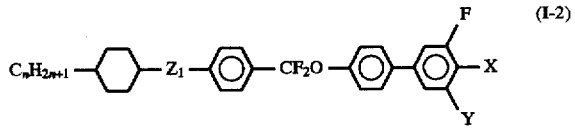
(I-2)

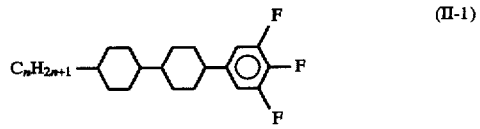
(II-1)

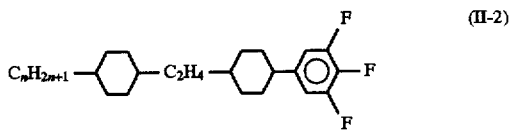
(II-2)

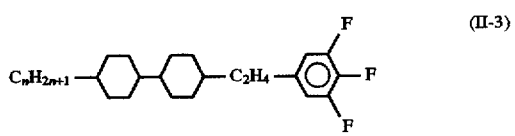
(II-3)

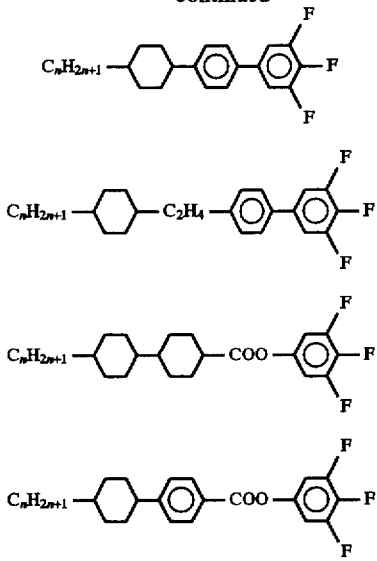

wherein n is an integer of 1 to 10, $Z_1$ represents —$CH_2CH_2$— or single bond, X represents F, $OCF_3$, or $CF_3$, and Y represents H or F.

2. The liquid crystal composition according to claim 1 wherein the amount of the first component is 3 to 50% by weight and the amount of the second component is 50 to 97% by weight based on the total weight of the liquid crystal composition, respectively.

3. The liquid crystal composition according to claim 1 or 2 wherein the liquid crystal composition further contains a compound expressed by general formula (III)

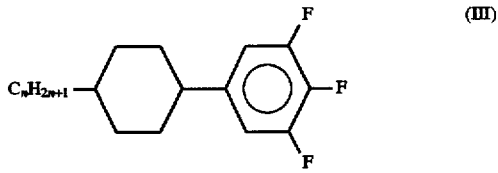

wherein n is an integer of 1 to 10.

4. The liquid crystal composition according to claim 1 or 2 wherein the liquid crystal composition further contains a compound expressed by general formula (IV-1) and/or general formula (IV-2)

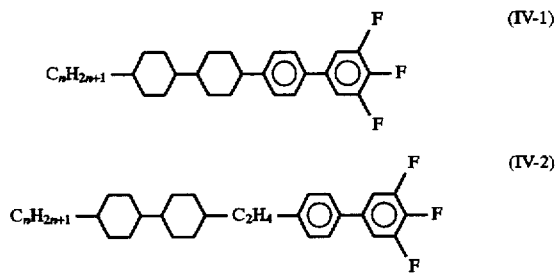

wherein n is an integer of 1 to 10.

5. The liquid crystal composition according to claim 1 or 2 wherein the liquid crystal composition further contains a compound expressed by general formula (V-1) and/or general formula (V-2)

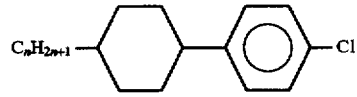

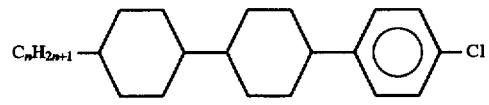

wherein n is an integer of 1 to 10.

6. A liquid crystal display device having used a liquid crystal composition defined in claim 1 or 2.

7. The liquid crystal composition according to claim 3 wherein the liquid crystal composition further contains a compound expressed by general formula (IV-1) and/or general formula (IV-2)

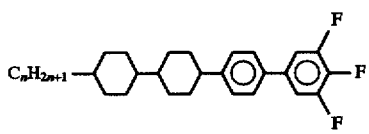

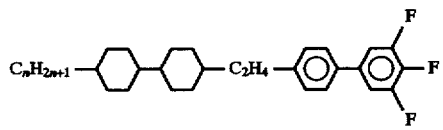

wherein n is an integer of 1 to 10.

8. The liquid crystal composition according to claim 3 wherein the liquid crystal composition further contains a compound expressed by general formula (V-1) and/or general formula (V-2)

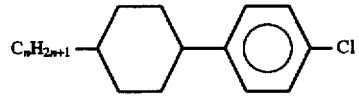

wherein n is an integer of 1 to 10.

9. The liquid crystal composition according to claim 4 wherein the liquid crystal composition further contains a compound expressed by general formula (V-1) and/or general formula (V-2)

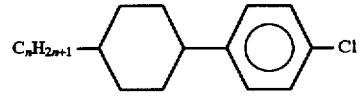

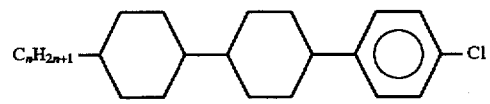

wherein n is an integer of 1 to 10.

10. The liquid crystal composition according to claim 7 wherein the liquid crystal composition further contains a compound expressed by general formula (V-1) and/or general formula (V-2)

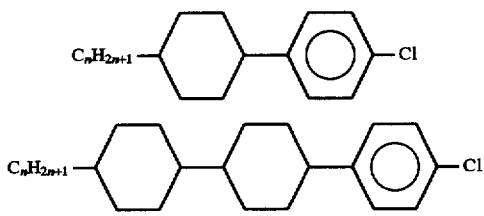

wherein n is an integer of 1 to 10.

11. A liquid crystal display device having used a liquid crystal composition defined in claim 3.

12. A liquid crystal display device having used a liquid crystal composition defined in claim 4.

13. A liquid crystal display device having used a liquid crystal composition defined in claim 5.

14. A liquid crystal display device having used a liquid crystal composition defined in claim 7.

15. A liquid crystal display device having used a liquid crystal composition defined in claim 8.

16. A liquid crystal display device having used a liquid crystal composition defined in claim 9.

17. A liquid crystal display device having used a liquid crystal composition defined in claim 10.

* * * * *